(12) United States Patent
Suda et al.

(10) Patent No.: US 8,067,393 B2
(45) Date of Patent: Nov. 29, 2011

(54) SUGAR-IMMOBILIZED METAL NANOPARTICLE, METHOD FOR MEASURING SUGAR-PROTEIN INTERACTION USING THE SAME AND METHOD FOR RECOVERING PROTEIN FROM SUGAR-PROTEIN INTERACTANT

(75) Inventors: Yasuo Suda, Kagoshima (JP); Tomoaki Nishimura, Hyogo (JP); Yuko Kishimoto, Hyogo (JP); Hiromi Nakagawa, Shizuoka (JP)

(73) Assignees: Japan Science and Technology Agency, Saitama (JP); National University Corporation Kagoshima University, Kagoshima (JP)

( * ) Notice: Subject to any disclaimer, the term of this patent is extended or adjusted under 35 U.S.C. 154(b) by 879 days.

(21) Appl. No.: 11/920,878

(22) PCT Filed: May 26, 2006

(86) PCT No.: PCT/JP2006/310592
§ 371 (c)(1), (2), (4) Date: Nov. 20, 2007

(87) PCT Pub. No.: WO2006/126689
PCT Pub. Date: Nov. 30, 2006

(65) Prior Publication Data
US 2009/0240032 A1    Sep. 24, 2009

(30) Foreign Application Priority Data
May 26, 2005   (JP) ................................. 2005-154550

(51) Int. Cl.
| | |
|---|---|
| A01N 43/04 | (2006.01) |
| A61K 31/715 | (2006.01) |
| G01N 33/00 | (2006.01) |
| C13K 5/00 | (2006.01) |
| C13K 7/00 | (2006.01) |

(52) U.S. Cl. ........................ 514/53; 436/86; 536/123.13
(58) Field of Classification Search ........................ None
See application file for complete search history.

(56) References Cited

U.S. PATENT DOCUMENTS
| | | | |
|---|---|---|---|
| 7,320,867 B2 | 1/2008 | Suda et al. | |
| 2008/0145838 A1* | 6/2008 | Suda et al. | 435/5 |
| 2009/0060839 A1* | 3/2009 | Boyes et al. | 424/9.1 |

FOREIGN PATENT DOCUMENTS
| | | |
|---|---|---|
| EP | 1538156 A1 | 6/2005 |
| JP | 2004-157108 | 6/2004 |
| JP | 2004-194669 | 7/2004 |
| JP | 2004-333232 | 11/2004 |
| JP | 2005-069955 | 3/2005 |
| JP | 2006-112980 | 4/2006 |
| WO | WO-2004/022583 A1 | 3/2004 |

OTHER PUBLICATIONS

De La Fuente, J. M. et al. (2004). "Understanding Carbohydrate-Carbohydrate Interactions by Means of Glyconanotechnology," *Glycoconjugate Journal* 21:149-163.
Sihelnikova, L. et al. (2007). "Step by Step Towards Understanding Gold Glyconanoparticles as Elements of the Nanoworld," *Chemical Papers* 61(4):237-255.
Supplementary European Search Report mailed Feb. 3, 2009, for EP Application No. 06746921.3 filed May 26, 2006, 9 pages.
Takae, S. et al. (2005). "Ligand Density Effect on Biorecognition by PEGylated Gold Nanoparticles: Regulated Interaction of RCA120 Lectin with Lactose Installed to the Distal End of Tethered PEG Strands on Gold Surface," *Biomacromolecules* 6(2):818-824.
Zhang, J. et al. (2004). "Complexation of Polysaccharide and Monosaccharide with Thiolate Boronic Acid Capped on Silver Nanoparticle," *Analytical Biochemistry* 332:253-260.
Brust, M. et al. (1994). "Synthesis of Thiol-Derivatised Gold Nanoparticles in a Two Phase Liquid-Liquid System," *Journal of the Chemical Society, Chemical Communications*, pp. 801-802.
CMC Technical Library 146. (Aug. 31, 1990). *Development and Evaluation of Bio Diagnostic Agents, and Companies Thereof.* First Edition, CMC Publishing Co., Ltd., pp. 92-97, 108-113. (partial English translation attached, 4 pages).
De La Fuente, J. M. et al. (2001). "Gold Glyconanoparticles as Water-Soluble Polyvalent Models to Study Carbohydrate Interactions," *Angewandte Chemie International Edition* 40(12): 2258-2261.
Feizi, T. et al. (2003). "Carbohydrate Microarrays—A New Set of Technologies at the Frontiers of Glycomics," *Current Opinion in Structural Biology* 13:637-645.
International Search Report mailed Jun. 27, 2006, for PCT Application No. PCT/JP2006/310592 filed May 26, 2006, 3 pages.
Otsuka, H. et al. (2001). "Quantitative and Reversible Lectin-Induced Association of Gold Nanoparticles Modified with Alpha-Lactosyl-Omega-Mercapto-Poly(Ethylene Glycol)," *Journal of the American Chemical Society* 123:8226-8230.
Schwarz, M. et al. (2003). "A New Kind of Carbohydrate Array, its Use for Profiling Antiglycan Antibodies, and the Discovery of a Novel Human Cellulose-Binding Antibody," *Glycobiology* 13(11):749-754.
Stoll, M. S. et al. (2000). "Fluorescent Neoglycolipids: Improved Probes for Oligosaccharide Ligand Discovery," *European Journal of Biochemistry* 267:1795-1804.

* cited by examiner

*Primary Examiner* — Marcela M Cordero Garcia
(74) *Attorney, Agent, or Firm* — Morrison & Foerster LLP

(57) ABSTRACT

It is intended to provide a stable novel sugar-immobilized metal nanoparticle capable of easily immobilizing a sugar chain, a method for measuring sugar-protein interaction easily and at a low cost using the same without labeling, and a method for simply recovering a protein from a sugar-protein interactant. A maltose-immobilized gold nanoparticle was obtained by binding a ligand complex, in which maltose and a linker compound had been bound to each other, to a gold nanoparticle. By adding this maltose-immobilized gold nanoparticle to a dilution series of concanavalin A, a sugar-protein interactant of maltose and ConA was formed, and red-purple color derived from a colloidal solution of maltose-immobilized gold nanoparticle disappeared. That is, sugar-protein interaction could be confirmed by visual observation without labeling.

4 Claims, 20 Drawing Sheets

SUGAR-IMMOBILIZED METAL NANOPARTICLE, METHOD FOR MEASURING SUGAR-PROTEIN INTERACTION USING THE SAME AND METHOD FOR RECOVERING PROTEIN FROM SUGAR-PROTEIN INTERACTANT

CROSS REFERENCE TO RELATED APPLICATIONS

This application is a U.S. National Phase application of International Application No. PCT/JP2006/310592, with an international filing date of May 26, 2006, which claims priority to Japanese Patent Application No. 2005-154550 filed on May 26, 2005, all of which are incorporated herein by reference in their entirety.

TECHNICAL FIELD

The present invention relates to a novel sugar-immobilized metal nanoparticle, a method for measuring sugar-protein interaction using same, and a method for recovering a protein from a sugar-protein interactant. The invention particularly relates to a novel sugar-immobilized metal nanoparticle in which a ligand complex having a linker compound bound to a sugar with a reducing end is bound to a metal nanoparticle, a method for measuring sugar-protein interaction using the sugar-immobilized metal nanoparticle without labeling, and a method for recovering a protein from a sugar-protein interactant based on conditions in which the aggregation of the sugar-protein interactant dissociates.

BACKGROUND ART

The interaction of sugar and protein (hereinafter "sugar-protein interaction") is an area of study that has been looked at with interest in structural biology for better understanding of cell-cell, cell-extracellular matrix, and cell-pathogen interactions.

Generally, sugar-protein interaction is analyzed through labeling of ligand proteins or conjugate sugars with radioactive isotopes or enzymes. For example, in ELISA or blotting methods, there have been techniques that use sugar chains labeled by pyridyl amination or fluorescence, or proteins labeled with secondary antibodies. As a method that analyzes sugar-protein interaction using sugar chains labeled by pyridyl amination or fluorescence, there is a method in which fluorescent sugar chains with pyridylamine are used to measure sugar-protein interaction by TLC (thin layer chromatography) or HPLC (high-pressure liquid chromatography) (Non-Patent Publication 1). As a method that analyzes sugar-protein interaction using proteins that have been labeled with secondary antibodies or the like, there is a method that uses labeled secondary antibodies to measure fluorescence in arrays (Non-Patent Publication 2).

As examples of a method that does not use a label, there have been available surface plasmon resonance (hereinafter, "SPR") and quarts crystal microbalance (hereinafter, "QCM").

SPR is a method in which a ligand complex including an oligosaccharide that mimics part of the sugar is introduced onto a surface of a sensor chip, which is then used to specify substances, such as proteins, that specifically interact with the oligosaccharide. QCM measures sugar-protein interaction by measuring changes in oscillation frequency of the crystal oscillator disturbed by adhesion of some material, by taking advantage of the characteristics of the crystal oscillator that the oscillation of the crystal oscillator under AC voltage remains constant unless it is disturbed by external factors.

There have been many reports concerning synthesis techniques for the immobilization of sugars, including a method in which a sugar chain modified with an aromatic amino group is bound to an aldehyde group in a metal colloid by reductive amination (Non-Patent Publication 3), and a method in which a compound with a thiol group for conjugation with a metal colloid is bound to a sugar chain by glycosylation (trichloroacetimidate method) (Non-Patent Publication 4)

[Non-Patent Publication 1]
M. S. Stoll et al., Eur. J. Biochem. 267, 1795-1804, 2000
[Non-Patent Publication 2]
M. Schwarz et al., Glycobiol. 13, no. 11, 749-754, 2003
[Non-Patent Publication 3]
H. Otsuka et al., J. Am. Chem. Soc. 123, 8226-8230, 2001
[Non-Patent Publication 4]
J. M. de la Fuente et al., Angew. Chem. Int. Ed. 40, No. 12, 2258-2260, 2001

A problem of the method that measures sugar-protein interaction using labeled sugar chains or proteins, however, is that it requires labeling as a pre-treatment and the effect of labeling greatly influences measurement variations. Further, while non-labeling methods have been available, the SPR or QCM requires very expensive equipment, which has made it difficult to perform measurement conveniently.

Further, it has been difficult to readily immobilize sugar chains due to the very complicated procedures required for the synthesis and purification, as exemplified by the method of Non-Patent Publication 3 which requires a pre-treatment for the sugar chain that has incorporated therein an aromatic amino group, and by the method of Non-Patent Publication 4 which requires at least five steps for the synthesis.

Further, while the method of evaluating sugar chains based on protein has been used for some time as a technique of analyzing sugar-protein interaction, it is not common to evaluate proteins based on sugar chain. Further, while it would be highly economical, no method has been available that enables a protein to be recovered from a sugar-protein interactant formed by the interaction of sugar and protein.

The present invention was made in view of the foregoing problems, and an object of the invention is to provide a novel sugar-immobilized metal particle that is stable and can readily immobilize a sugar chain, a method for measuring sugar-protein interaction both easily and inexpensively without labeling, using the sugar-immobilized metal particle, and a method for conveniently recovering a protein from a sugar-protein interactant.

DISCLOSURE OF INVENTION

The inventor of the present invention diligently worked to accomplish the above object, and found that a sugar-immobilized metal nanoparticle in which a ligand complex having a linker compound bound to a sugar with a reducing end by reductive amination is bound to a metal is stable and can readily immobilize a sugar chain.

Further, the inventor measured sugar-protein interaction easily without labeling, only through mixture of the sugar-immobilized metal nanoparticle with a protein. In addition, the inventor found that a protein can be recovered very easily from the sugar-protein interactant by changing a pH of the suspension of the interactant, and mixing the sugar-protein interactant with a sugar chain that is recognizable by the protein, and accomplished the present invention.

That is, a sugar-immobilized metal nanoparticle of the present invention includes: a ligand complex of a structure including a linker compound and a sugar having a reducing end, the linker compound including a hydrocarbon structure which includes: a hydrocarbon inducing chain with an amino group at an end and optionally a carbon-nitrogen bond in a backbone; and a sulfur atom, the sugar being bound to the linker compound via the amino group; and a metal bound to the ligand complex.

The hydrocarbon inducing chain denotes a hydrocarbon inducing chain in which a hydrocarbon chain constituted by carbon and hydrogen includes carbon atoms or hydrogen atoms part of which can be substituted by other atom or a substituent. That is, the hydrocarbon inducing chain denotes a hydrocarbon inducing chain which has an amino group at an end and a carbon-carbon bond (C—C bond) in a backbone, part of which can be substituted with a carbon-nitrogen bond (C—N bond), a carbon-oxygen bond (C—O bond), an amide bond (CO—NH bond).

The hydrocarbon structure including a sulfur atom means a hydrocarbon structure which is constituted by carbon and hydrogen and in which a part of carbon atoms is substituted with a sulfur atom. Further, the hydrocarbon structure including a sulfur atom may be a chain structure (including both a straight-chain structure and branched chain structure), a cyclic structure, or a structure including both the chain structure and the cyclic structure.

The sugar-immobilized metal nanoparticle of the present invention may be such that the hydrocarbon structure including a sulfur atom includes a S—S bond or an SH bond. In other words, the hydrocarbon structure including a sulfur atom may include a disulfide bond (S—S bond) or a thiol group (SH bond).

The sugar-immobilized metal nanoparticle of the present invention is preferably such that the amino group is an aromatic amino group. At a pH in the range from 3 to 4 that is optimum conditions for reductive amination, it is necessary that an amino group is not protonated. Therefore, an aromatic amino group is preferable in which a non-covalent electron pair is present on a nitrogen atom due to aromatic conjugation even at a pH in the range from 3 to 4.

The sugar-immobilized metal nanoparticle of the present invention is preferably such that the metal is gold.

According to the above structure, bonding with an arbitrary metal can be made by the S—S bond in the linker compound, which forms a metal-sulfur (S) bond such as a gold-sulfur (Au—S) bond, for example. In this way, a sugar-immobilized metal nanoparticle can be realized via the Au—S bond.

A method for measuring sugar-protein interaction according to the present invention, includes the step of forming a sugar-protein interactant through interaction of sugar and protein by mixing a solution containing the sugar-immobilized metal nanoparticle of the present invention with a protein that recognizes the sugar situated at the end of the sugar-immobilized metal nanoparticle.

According to the above method, a protein recognizes a sugar situated at an end of the sugar-immobilized metal nanoparticle, whereupon hydrogen bonding or other sugar-protein interaction occur. This makes it possible to measure sugar-protein interaction conveniently without labeling, and also possible to measure sugar-protein interaction simply by visually observing an aggregation reaction.

A method for recovering a protein from a sugar-protein interactant according to the present invention, includes the steps of: forming a sugar-protein interactant through interaction of sugar and protein by mixing a solution containing the sugar-immobilized metal nanoparticle of the present invention with a protein that recognizes the sugar situated at the end of the sugar-immobilized metal nanoparticle; and adjusting a pH of an admixture solution of the sugar-protein interactant and water to 5 or less.

According to the above method, because the admixture solution is acidic, the protein can be detached from the sugar chain moiety of the sugar-protein interactant. Further, because the admixture solution at a pH of 5 or less denatures the structure of the protein constituting the sugar-protein interactant and thereby attenuates the capability of the sugar to recognize the protein, the protein can be completely dissociated from the sugar-protein interactant. Therefore, it is possible to easily recover the protein from the sugar-protein interactant.

A method for recovering a protein from a sugar-protein interactant according to the present invention, includes the steps of: forming a sugar-protein interactant through interaction of sugar and protein by mixing a solution containing the sugar-immobilized metal nanoparticle of the present invention with a protein that recognizes the sugar situated at the end of the sugar-immobilized metal nanoparticle; and mixing the sugar-protein interactant with a sugar that is recognizable by the protein.

According to the above method, a substitution reaction occurs between the protein constituting the sugar-protein interactant and the sugar that is recognizable by the protein. This enables the protein to dissociate from the sugar-protein interactant as a result of this reaction. Therefore, it is possible to easily recover the protein from the sugar-protein interactant.

Additional objects, features, and strengths of the present invention will be made clear by the description below. Further, the advantages of the present invention will be evident from the following explanation in reference to the drawings.

BEST MODE FOR CARRYING OUT THE INVENTION

Figure 1:
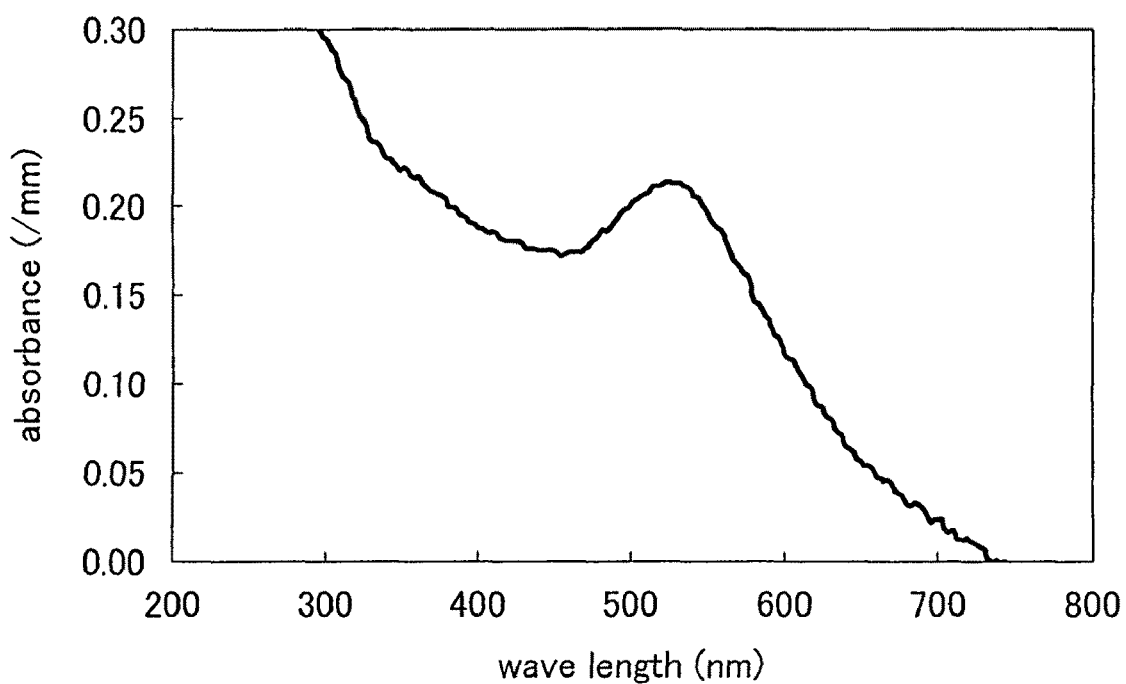
FIG. 1 is an ultraviolet-visible absorption spectrum of a colloid solution of maltose-immobilized gold nanoparticles.

The following will describe an embodiment of the present invention. The present invention is not limited in any ways by the following description. Described below are a sugar-immobilized metal nanoparticle, a method for measuring sugar-protein interaction, and a method for recovering a protein from a sugar-protein interactant according to the present invention.

(1) Sugar-Immobilized Metal Nanoparticle

The "sugar-immobilized metal nanoparticle" as used herein denotes a structure including a ligand complex, described below, bound to an arbitrary metal.

The ligand complex as a constituting member of a sugar-immobilized metal nanoparticle according to the present invention includes: a linker compound bindable to an arbitrary metal; and a sugar chain that can specifically interact with proteins or other substances to be analyzed. It is therefore required that the ligand complex do not show non-specific interaction with substances such as proteins.

To this end, a ligand complex of the present invention includes a sulfur atom (S), which can strongly bind to a metal by, for example, forming a metal-sulfur bond (Au—S bond) with gold (Au) dispersed in a colloid solution.

The linker compound also includes a hydrocarbon inducing chain that includes an amino group at an end and optionally a carbon-nitrogen bond in the backbone. This enables the linker compound to arrange a sugar molecule in clusters, and, with the amino group at an end, readily incorporate the sugar molecule. The amino group may be modified or unmodified. For example, the amino group may be modified with an acetyl group, a methyl group, or a formyl group.

For ease of forming a metal-sulfur bond (Au—S bond), the linker compound preferably includes a hydrocarbon structure including a S—S bond or an SH bond. The sulfur (S) in the disulfide bond (S—S bond) or SH bond can form, for example, a metal-sulfur bond (Au—S bond) with gold (Au) dispersed in the colloid solution, thereby strongly binding to the metal in the colloid solution.

At the amino group of the linker compound, the ligand complex incorporates a sugar chain having a reducing end. In other words, the ligand complex has a structure with the linker compound attached via the amino group to the sugar having a reducing end. The sugar can be incorporated by reductive amination of the sugar and the amino group (—NH$_2$ group) of the linker compound, for example. Specifically, the aldehyde group (—CHO group) or ketone group (—CRO group, R being a hydrocarbon group) generated in the sugar at equilibrium reacts with the amino group of the linker compound. By the subsequent reduction of the Schiff base formed by the reaction, the sugar is readily incorporated at the amino group.

The "sugar having a reducing end" herein denotes a monosaccharide or oligosaccharide with no substitution of the anomeric carbon atom. The sugar having a reducing end may be commercial products or natural products. Alternatively, the sugar having a reducing end may be prepared through degradation and synthesis from commercial or natural polysaccharides.

Specific examples of the sugar having a reducing end include, but are not limited to, glucose, galactose, mannose, maltose, isomaltose, lactose, panose, cellobiose, melibiose, mannoligosaccharide, chitoligosaccharide, laminariolgosaccharide, glucosamine, N-acetyl glucosamine (hereinafter "GlcNAc"), glucuronic acid, sulfated oligosaccharide, sialic acid, various antigen sugar chains, N-acetyl galactosamine, fucose, maltotriose, isomaltotriose, gentiobiose, fucosyl lactose, chitobiose, and globobiose.

The linker compound of the ligand complex includes a sulfur atom bindable to metal, and an amino group bindable to a sugar molecule such as an oligosaccharide chain. This enables the ligand complex to be immobilized on a metal through a metal-sulfur bond, for example, such as a Au—S bond, thereby strongly and readily binding the sugar molecule to a sugar-immobilized metal nanoparticle of the present invention via the linker compound, and stabilizing the sugar-immobilized metal nanoparticle in the solution. Further, since the ligand complex can be bound to the metal simply by mixing it with a solution containing the metal, the sugar chain can be immobilized very easily.

Further, the ligand complex is almost free from the influence of non-specific interaction with protein. Thus, with the ligand complex including the linker compound, the interaction between sugar and protein can be evaluated with good reproducibility.

The linker compound is produced by the following method, for example. Specifically, the linker compound is produced by the condensation reaction of thioctic acid at an end of the aromatic amino group.

The condensation reaction of thioctic acid with the aromatic amino group forms an amido bond by the condensation of the carboxy group (—COOH group) of the thioctic acid with the aromatic amino group, with the result that the linker compound is obtained.

The ligand complex includes the linker compound and the sugar having a reducing end that has been incorporated in the linker compound.

Because the ligand complex includes the linker compound and the sugar molecule, bonding with an arbitrary metal can be made by the S—S bond in the linker compound, which forms a metal-sulfur (S) bond such as a gold-sulfur (Au—S) bond, for example. In this way, a sugar-immobilized metal nanoparticle can be realized in which the sugar molecule is immobilized on metal via the Au—S bond. The metal may be any metal as long as it is bindable to the ligand complex. Other than gold, the metal may be copper, silver, or platinum, for example. Gold is particularly preferable, however. Considering availability, gold is preferably chloroauric acid and its salt, and particularly sodium chloroaurate.

The sugar incorporated in the ligand complex may be any sugar as long as it has a reducing end. For example, the sugar may be a monosaccharide, a homooligosaccharide composed of the same type of simple sugar molecules, or a conjugate sugar composed of various types of simple sugar molecules and their derivatives. Further, the sugar may be a variety of natural sugars isolated and purified from nature, or synthetic sugars. Further, the sugar may be obtained through degradation of polysaccharides.

A sugar-immobilized metal nanoparticle according to the present invention may be obtained by mixing the ligand complex with a solution containing metal, whereby each sulfur atom of the S—S bond in the ligand complex binds to metal by forming a metal-sulfur bond. In one specific example, the sugar-immobilized metal nanoparticle may be obtained by mixing a colloid solution of metal with a solution containing the ligand complex and by stirring the admixture to convert the S—S bond of the ligand complex to a metal-sulfur bond with the metal, such as gold, contained in the colloid solution.

Note that, when the solution contains the metal in the form of a salt, it is preferable to reduce the metal with a reducing agent, prior to mixing the solution with the ligand complex. This facilitates bonding of the metal with the ligand complex. The reducing agent is not particularly limited. Some of the examples include sodium borohydride, ascorbic acid and its salt, phosphorous, tannic acid and its salt, ethanol, and hydrazine.

The dispersion medium of the metal solution, and the solvent used for the solution containing the ligand complex are not particularly limited. For example, methanol, water, or a mixed solvent of methanol and water may be used. The sugar-immobilized metal nanoparticle obtained from the admixture may be dialyzed to remove low-molecular-weight salts. In this way, the sugar-immobilized metal nanoparticle can assume a stable state in a solution.

The mixing ratios of the metal, reducing agent, and ligand complex used to prepare the sugar-immobilized metal nanoparticle are not particularly limited. When the metal is chloroauric acid and its salt, it is preferable that the final concentration of chloroauric acid and its salt in the solution be 0.5 mM to 4 mM, and more preferably 1 mM to 2 mM.

The final concentration of the reducing agent in the solution is preferably 3 to 10 times, and more preferably 4 to 5 times the molar concentration of the gold ion.

The final concentration of the ligand complex in the solution is preferably 10 µM to 1000 µM, and more preferably 50 µM to 150 µM.

(2) A Method for Measuring Sugar-Protein Interaction

A method for measuring sugar-protein interaction according to the present invention includes the step of forming a sugar-protein interactant through interaction of sugar and protein by mixing a solution containing a sugar-immobilized metal nanoparticle with proteins that recognize the sugar situated at an end of the sugar-immobilized metal nanoparticle.

As used herein, the "solution containing a sugar-immobilized metal nanoparticle" is intended to mean a liquid dispersing a sugar-immobilized metal nanoparticle according to the present invention. The liquid may additionally include other substances such as salts, so long as the sugar-immobilized metal nanoparticle is contained. Examples of the liquid are water and buffer.

The protein is not particularly limited as long as it can recognize the sugar situated at an end of the sugar-immobilized metal nanoparticle. For example, when the sugar situated at an end of the sugar-immobilized metal nanoparticle is glucose, proteins that can recognize glucose may be used, for example, such as concanavalin A (ConA), lentil lectin (LCA), and peanut lectin (PNA).

When the sugar situated at an end of the sugar-immobilized metal nanoparticle is galactose, proteins that can recognize galactose may be used, for example, such as caster bean lectin (RCA120). When the sugar situated at an end of the sugar-immobilized metal nanoparticle is N-acetyl glucosamine, proteins that can recognize N-acetyl glucosamine may be used, for example, such as wheat germ lectin (WGA).

Various other proteins that recognize other sugar chains may be used. Non-limiting examples are *Dolichos biflorus* lectin (BPA), *Maackia amurensis* lectin (MAM), *Sambucus sieboldiana* lectin, (SSA), *Pisum sativum* lectin (PSA), Jacalin (JAC), *Griffonia simplicifolia* lectin (GS-II), and *Ulex europaeus* lectin (UEA-I).

The method of mixing the solution containing a sugar-immobilized metal nanoparticle with proteins that recognize the sugar situated at an end of the sugar-immobilized metal nanoparticle is not particularly limited as long as it can cause interaction of sugar and protein. For example, a dilution series of protein may be prepared in a microplate or an Eppendorf tube, and a solution containing a sugar-immobilized metal nanoparticle may be added thereto and left to stand therein.

The interaction of sugar and protein (sugar-protein interaction) may be hydrogen bonding, ionic bonding, electrostatic interaction, or Van der Waals attraction, for example. More specifically, the protein recognizes the sugar situated at an end of the sugar-immobilized metal nanoparticle, whereupon hydrogen bonding or other sugar-protein interactions occur.

The term "recognize" as used herein refers to the binding of the protein to the sugar chain at the sugar binding site (sugar chain recognition site) present within the protein molecule.

The "sugar-protein interactant" as used herein is intended to mean an aggregate resulting from the interaction and specific binding of sugar and protein. With a method for measuring sugar-protein interaction according to the present invention, the sugar-protein interaction can be visually confirmed using formation of the sugar-protein interactant as an indicator. The sugar-protein interactant is not formed when there is no interaction of sugar and protein.

As a method that measures interaction of substances by confirming an aggregation reaction, a latex aggregation method using antigen-antibody reaction is available, for example (*Development of Bio-Diagnosis, its Evolution and Related Company*, CMC Technical Library 146, CMC Publishing Co., Ltd., p. 92-97, p. 109-113). In the latex aggregation method, antibodies are immobilized on a latex surface, and a dilution series of sample antigens is prepared using a 96-well microplate. This is followed by determination of a maximum dilution factor at which aggregation occurs, which is then compared with a standard solution for the measurement. Results are given by measuring absorbance at a certain wavelength of light.

However, as to a method that measures interaction of substances by confirming an aggregation reaction in colloids, the only method known is the technique in which results are based on colors imparted by the particles, or more specifically red imparted by relatively small particles, and purple imparted by relatively large particles. In this regard, a method according to the present invention is highly convenient and useful over the conventional methods because results are given by the confirmation of aggregate formation which is enabled also in colloids by the interaction of sugar and protein.

A method according to the present invention measures sugar-protein interaction without labeling. This is very convenient because it does not require a pre-treatment as required in methods employing labeling. Further, the method does not have the problem of labeling, which strongly affects measurement variations, thereby enabling measurement with good reproducibility. Further, since sugar-protein interaction can be visually confirmed, the measurement of sugar-protein interaction does not require any special equipment, enabling the measurement to be performed at significantly low cost and conveniently.

A method according to the present invention is therefore usable for the functional analysis of sugars and proteins, as well as testing and diagnosis.

Note that, a method for measuring sugar-protein interaction according to the present invention may at least include the step of forming a sugar-protein interactant through interaction of sugar and protein by mixing a solution containing a sugar-immobilized metal nanoparticle with proteins that recognize the sugar situated at an end of the sugar-immobilized metal nanoparticle. As such, formation of a sugar-protein interactant may simply be confirmed by visual inspection for example, or, when more detailed measurement is needed, the method may further include the step of measuring a UV-visible absorption spectrum at a certain wavelength.

(3) A Method for Recovering Protein from Sugar-Protein Interactant

In one embodiment, a method for recovering a protein from a sugar-protein interactant according to the present invention includes the steps of forming a sugar-protein interactant through interaction of sugar and protein by mixing a solution containing a sugar-immobilized metal nanoparticle with proteins that recognize the sugar situated at an end of the sugar-immobilized metal nanoparticle, and adjusting a pH of an admixture solution of the sugar-protein interactant and water to 5 or less.

The step of adjusting a pH of an admixture solution of the sugar-protein interactant and water to 5 or less is the step in which the sugar-protein interactant formed by the interaction of sugar and protein is recovered by a technique such as centrifugation, and in which the sugar-protein interactant so obtained is mixed with water and the pH of the admixture solution is adjusted to 5 or less using an acid. The acid is not particularly limited as long as it can make the admixture solution acidic. Some of the examples are hydrochloric acid, sinapinic acid, nitric acid, and sulfuric acid.

Because the admixture solution at a pH of 5 or less is acidic, the protein can be detached from the sugar chain moiety of the sugar-protein interactant. Further, because the admixture solution at a pH of 5 or less denatures the structure of the protein constituting the sugar-protein interactant and thereby attenuates the ability of the sugar to recognize the protein, the protein can be completely dissociated from the sugar-protein interactant.

The protein dissociated from the sugar-protein interactant clearly dissociates also from the sugar-immobilized metal nanoparticle, as will be described layer in Examples. This makes it possible to easily recover the protein. The protein so dissociated may be identified by a method such as acrylamide electrophoresis, protein quantification, or mass spectrometry. The mass spectrometry may be performed according to a conventionally known method using a conventionally known mass spectrometer such as the matrix assisted laser desorption/ionization, time of flight mass spectrometer (MALDI-TOF/MS).

In one embodiment, a method for recovering a protein from a sugar-protein interactant according to the present invention includes the steps of forming a sugar-protein interactant through interaction of sugar and protein by mixing a solution containing a sugar-immobilized metal nanoparticle with proteins that recognize the sugar situated at an end of the sugar-immobilized metal nanoparticle, and mixing the sugar-protein interactant with a sugar that is recognizable by the protein.

In the step of mixing the sugar-protein interactant with a sugar that is recognizable by the protein, the sugar-protein interactant formed by the interaction of sugar and protein is recovered by a technique such as centrifugation, and the sugar-protein interactant so obtained is mixed with a sugar that is recognizable by the protein constituting the sugar-protein interactant.

As a result, a substitution reaction occurs between the protein constituting the sugar-protein interactant and the sugar that is recognizable by the protein. It is believed that the protein dissociates from the sugar-protein interactant as a result of this reaction. The substitution reaction is not particularly limited. For example, it may be nucleophilic substitution reaction or electrophilic substitution reaction.

The method of mixing in the step of mixing the sugar-protein interactant with a sugar that is recognizable with the protein is not particularly limited, and the method may or may not be accompanied by stirring. The step involves a substitution based on affinity between the sugar of the sugar-protein interactant and the sugar that is recognizable by the protein. It is therefore preferable that the sugar that is recognizable by the protein is added in excess.

The dissociated protein may be identified by a method such as acrylamide electrophoresis, protein quantification, or mass spectrometry.

A more detailed analysis of the protein would be possible if aggregation due to the sugar-protein interaction could be inhibited by addition of various types of sugar chains that are recognizable by the protein in the reaction of the protein with the sugar-immobilized metal nanoparticle. For example, it would be possible to perform a functional analysis that determines which sugar chain is more apt to form a strong bond with the protein.

The present invention is not limited to the description of the embodiment above, but may be altered by a skilled person within the scope of the claims. An embodiment based on a proper combination of technical means disclosed in different embodiments is encompassed in the technical scope of the present invention.

EXAMPLES

The following will describe details of the present invention with reference to Examples and FIGS. 1 through 20. However, the present invention is not limited to the descriptions of Examples. The present invention may be varied, altered, modified, by a person skilled in the art within the scope of the present invention.

Example 1

Preparation of Maltose-Immobilized Gold Nanoparticles

Sodium chloroaurate (III) and sodium borohydride were vigorously stirred and mixed with water so that final concentrations of sodium chloroaurate (III) and sodium borohydride are 1 mM and 5 mM, respectively, thereby preparing a solution of gold nanoparticles. Ligand complex was a compound of thioctic acid, m-phenylenediamine, and maltose (molar ratio of 1:1:1). To the ligand complex, water was added to obtain a solution of ligand complex with a final concentration of 100 pM. The solution of ligand complex was added to the solution of gold nanoparticles. Then, the resulting mixture solution was vigorously stirred and mixed, thereby preparing a colloid solution of crude maltose-immobilized gold nanoparticles.

Next, the colloid solution of crude maltose-immobilized gold nanoparticles was transferred to a dialysis tube (MWCO:3,500) and subjected to dialysis with water and PBS-T (0.05%), thereby purifying the colloid solution to a colloid solution of maltose-immobilized gold nanoparticles. FIG. 1 shows an ultraviolet-visible absorption spectrum of the colloid solution of maltose-immobilized gold nanoparticles. As shown in FIG. 1, maximum absorption wavelength thereof was 525 nm.

Example 2

Measurement of Sugar-Protein Interaction

Dilution series (PBS-T (0.05%)) of concanavalin A (hereinafter referred to as "ConA"; manufactured by EY Laboratories Inc.), which is a protein that recognizes maltose, and dilution series (PBS-T (0.05%)) of bovine serum albumin (hereinafter referred to as "BSA"; manufactured by SIGMA), which is a non-maltose-recognizing protein, were placed at 10 µM and lower concentrations on 96-well titer plate (25 µl per well). Then, the colloid solution of maltose-immobilized gold nanoparticles was added to each of the diluents so that a ratio between the colloidal solution and the diluent is 1:1. The resulting mixture solution was left for 30 minutes to 2 hours. After aggregation of the maltose-immobilized gold nanoparticles was completed, the result was evaluated by visual observation and measurement of ultraviolet-visible absorption spectrum (540 nm).

Figure 2:
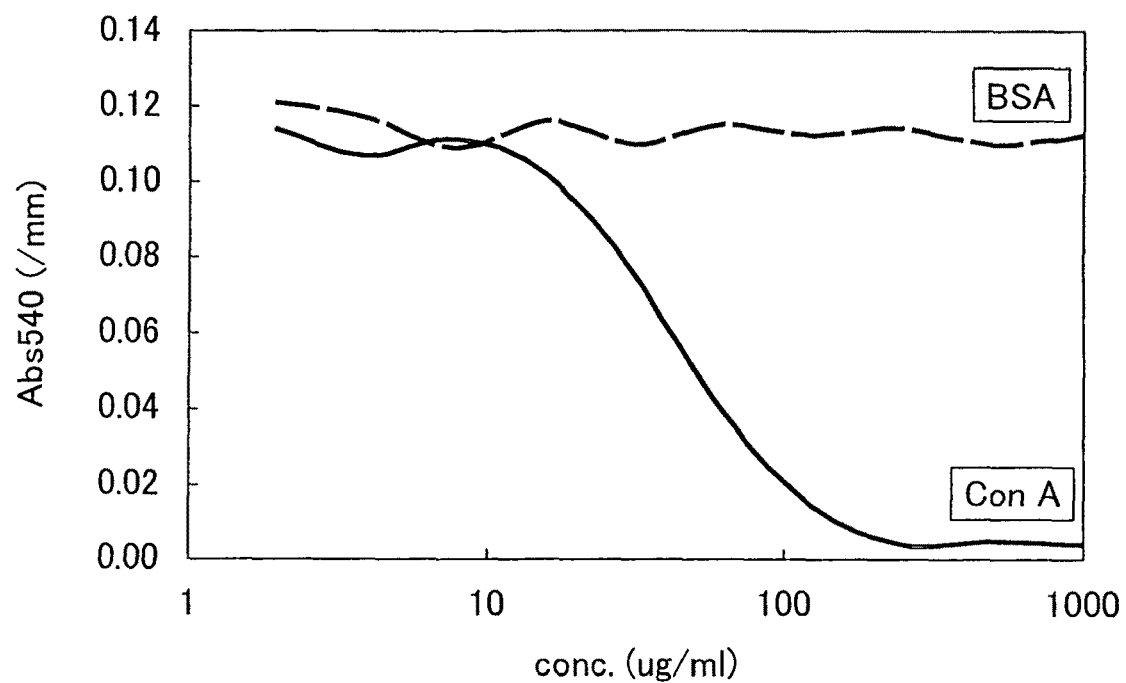
FIG. 2 is an ultraviolet-visible absorption spectrum showing sugar-protein interaction between maltose and ConA and sugar-protein interaction between maltose and BSA.
Figure 3:
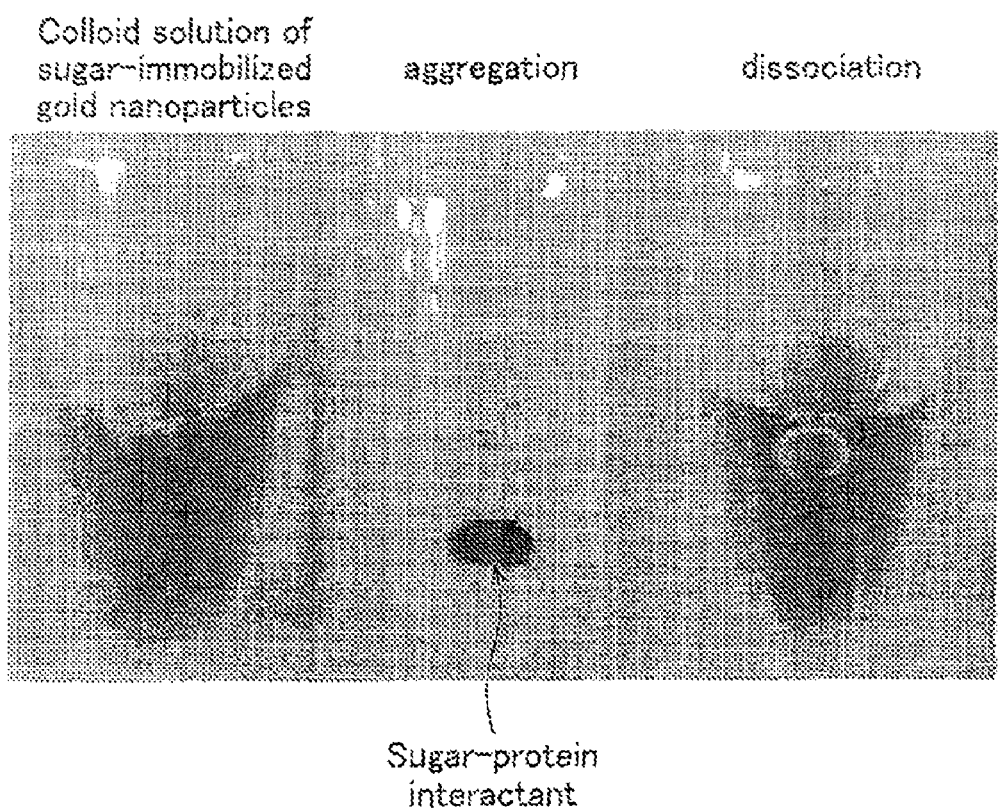
FIG. 3 is an illustration showing, from the left thereof, a photograph of a colloid solution of maltose-immobilized gold nanoparticles, a photograph of a sugar-protein interactant that is an aggregate caused by sugar-protein interaction, and a photograph of dissociation of a protein from the sugar-protein interactant by addition of glucose to the sugar-protein interactant.

FIG. 2 is an ultraviolet-visible absorption spectrum showing sugar-protein interaction between maltose and ConA and between maltose and BSA. A horizontal axis represents a concentration of ConA or BSA, and a longitudinal axis represents an absorbance at a wavelength of 540 nm. FIG. 3 shows, from the left thereof, a photograph of the colloid solution of maltose-immobilized gold nanoparticles, a photograph of a sugar-protein interactant that is an aggregate caused by sugar-protein interaction, and a photograph of dissociation of a protein from the sugar-protein interactant by addition of glucose to the sugar-protein interactant.

The finding from FIG. 2 is as follows: In a case where ConA was used, a sugar-protein interactant of maltose and ConA was produced by sugar-protein interaction and is an aggregate depending upon a concentration of ConA, whereby red-purple color (absorption at approximately 540 nm) derived from the colloid solution of maltose-immobilized gold nanoparticles disappeared. In a case where a concentration of the protein (ConA) that binds specifically to maltose was low, obtained absorption intensity was not different from that of the colloid solution of maltose-immobilized gold nanoparticles. On the other hand, in a case where the protein (BSA) that does not bind specifically to maltose was added, no aggregation occurred and ultraviolet-visible absorption spectrum remained almost unchanged.

The photograph in the center of FIG. 3 shows that sugar-protein interactant is an aggregate. Sugar is maltose, and protein is ConA. Thus, according to a sugar-protein interaction measurement method of the present invention, it is possible to confirm sugar-protein interaction with great ease by visual observation without labeling. Ultraviolet-visible absorption spectrum measurement produces specific findings as shown in FIG. 2.

Example 3

Recovery of ConA from Sugar-Protein Interactant

100 µl of PBS-T (0.05%) solution containing ConA at 250 µg/ml was placed in an Eppendorf tube. To the solution was added 100 µl of the colloid solution of maltose-immobilized gold nanoparticles which was prepared in Example 1. Then, a mixture solution was vortexed for at least 10 seconds. Thereafter, the resulting mixture solution was left for approximately 2 hours, and a sugar-protein interactant was precipitated out of the mixture solution by centrifugation. Then, supernatant thereof was removed, and the sugar-protein interactant was washed with PBS-T (0.05%) solution and water several times. After the washing, 100 µl of 200 mM glucose aqueous solution was added to the sugar-protein interactant, and the resulting mixture solution was left for approximately 1 hour. The result was evaluated by (i) visually observing return of ConA from the sugar-protein interactant to the colloid solution of maltose-immobilized gold nanoparticles due to dissociation of ConA from the sugar-protein interactant, and (ii) measuring ultraviolet-visible absorption spectrum.

The photograph on the left in FIG. 3 shows the colloid solution of maltose-immobilized gold nanoparticles, and the photograph in the center of FIG. 3 shows aggregation of the sugar-protein interactant. The photograph on the right in FIG. 3 shows that addition of glucose induced dissociation of ConA that has been bound selectively to maltose-immobilized gold nanoparticles, and color of the solution returned to red-purple color derived from the colloid solution of maltose-immobilized gold nanoparticles.

Figure 4:
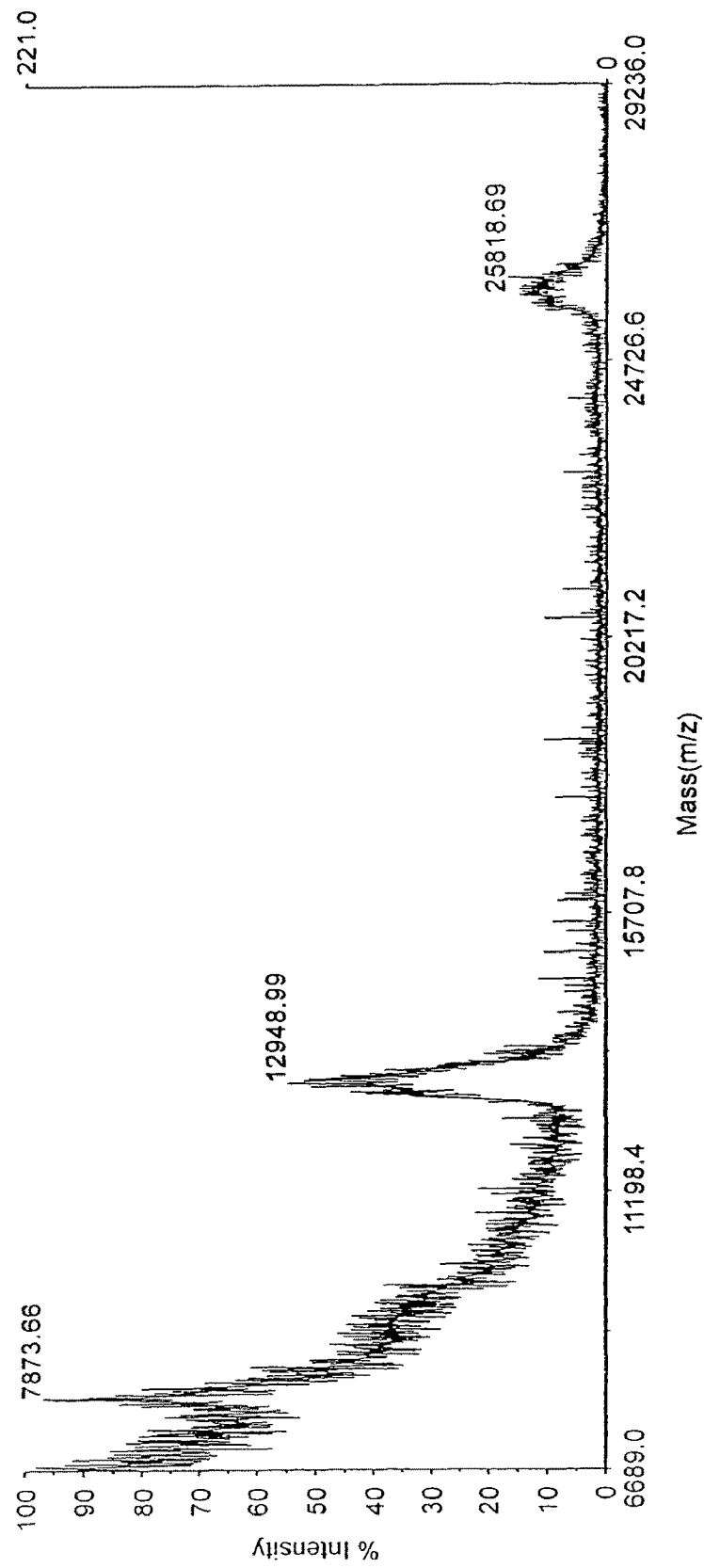
FIG. 4 is an illustration showing the result of MALDI-TOF/MS analysis of ConA contained in a colloid solution of maltose-immobilized gold nanoparticles after the dissociation.

Addition of a sugar chain which is not recognized by ConA does not induce dissociation of ConA. As a result of analysis of a protein contained in the colloid solution of maltose-immobilized gold nanoparticles obtained after the dissociation of ConA by SDS-PAGE and MALDI-TOF/MS (manufactured by Applied Biosystems (Applied Biosystems; VOYAGER-DE PRO), only ConA was detected. FIG. 4 is an illustration showing the result of MALDI-TOF/MS analysis of ConA contained in the colloid solution of maltose-immobilized gold nanoparticles after the dissociation, wherein three peaks at m/z values of 7873.66, 12948.99, and 25818.69 are peaks of ConA (fragments).

Example 4

Measurement of Various Sugar-Protein Interactions

In the present example, maltose, lactose, and chitobiose were immobilized for preparation of colloid solutions of sugar-immobilized gold nanoparticles. Sugar-protein interaction was measured by determining whether the colloid solution of sugar-immobilized gold nanoparticles bind specifically to lectin.

Sodium tetrachloroaurate (III) and sodium borohydride were vigorously stirred and mixed with water so that final concentrations of sodium tetrachloroaurate (III) and sodium borohydride are 1 mM and 5 mM, respectively, thereby preparing a solution of gold nanoparticles. Ligand complex was a compound of thioctic acid, m-phenylenediamine, and sugar. To the ligand complex, water was added to obtain a solution of ligand complex with a final concentration of 100 µM. The solution of ligand complex was added to the solution of gold nanoparticles. Then, the resulting mixture solution was vigorously stirred and mixed, thereby preparing a colloid solution of crude sugar-immobilized gold nanoparticles. The sugar was maltose, lactose, or chitobiose.

Next, the colloid solution of crude sugar-immobilized gold nanoparticles was transferred to a dialysis tube (MWCO:3, 500) and subjected to dialysis with water and PBS-T (0.05%), thereby purifying the colloid solution to a colloid solution of sugar-immobilized gold nanoparticles.

Next, dilution series (PBS-T (0.05%)) of concanavalin A (hereinafter referred to as "ConA"; manufactured by EY Laboratories Inc.), which is a protein that recognizes maltose, dilution series of caster bean lectin (RCA120; manufactured by Seikagaku Corporation), which is a lactose-recognizing protein, or wheat germ lectin (hereinafter referred to as WGA; manufactured by Seikagaku Corporation), which is a chitobiose-recognizing protein, and dilution series (PBS-T (0.05%)) of bovine serum albumin (hereinafter referred to as "BSA"; manufactured by SIGMA), which is a non-maltose-recognizing protein that does not recognize maltose, lactose, and chitobiose, were placed at 1 mg/ml and lower concentrations on 96-well titer plate (25 µl per well). Then, the colloid solution of sugar-immobilized gold nanoparticles was added to each of the diluents so that a ratio between the colloidal solution and the diluent is 1:1. The resulting mixture solution was left for 30 minutes to 2 hours. After aggregation of the sugar-immobilized gold nanoparticles was completed, the result was evaluated by visual observation and measurement of ultraviolet-visible absorption spectrum (540 nm).

Figure 5:
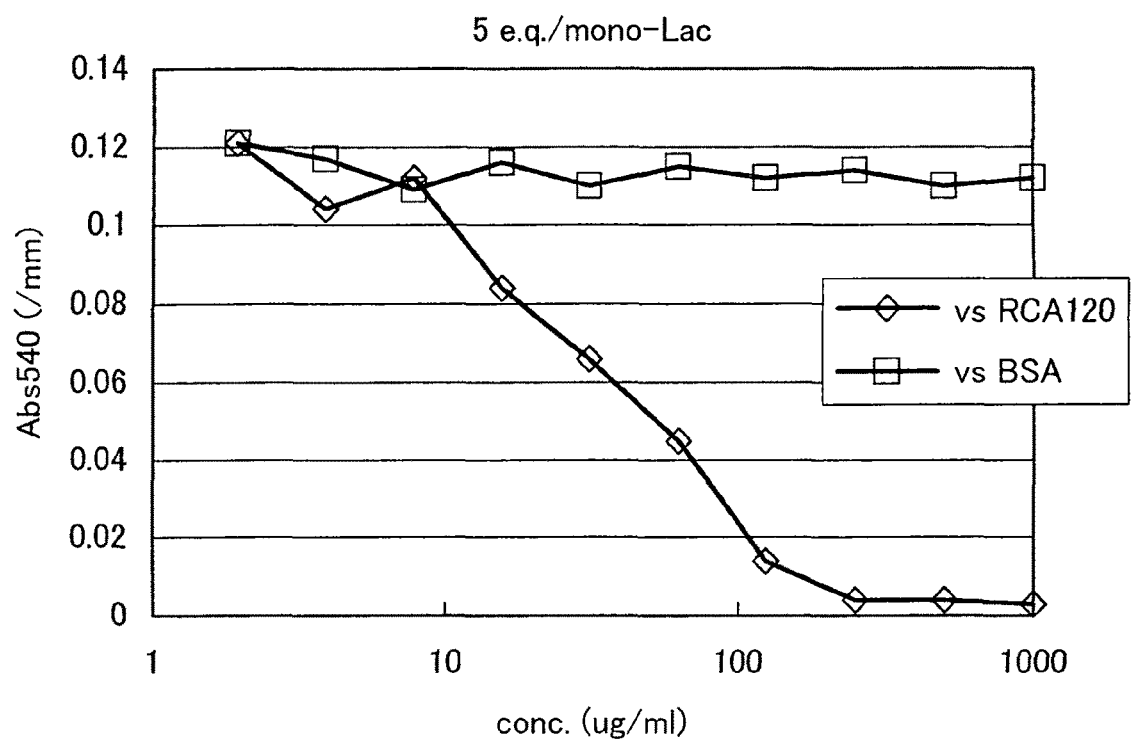
FIG. 5 is an ultraviolet-visible absorption spectrum showing sugar-protein interaction between lactose and RCA120 and sugar-protein interaction between lactose and BSA.
Figure 6:
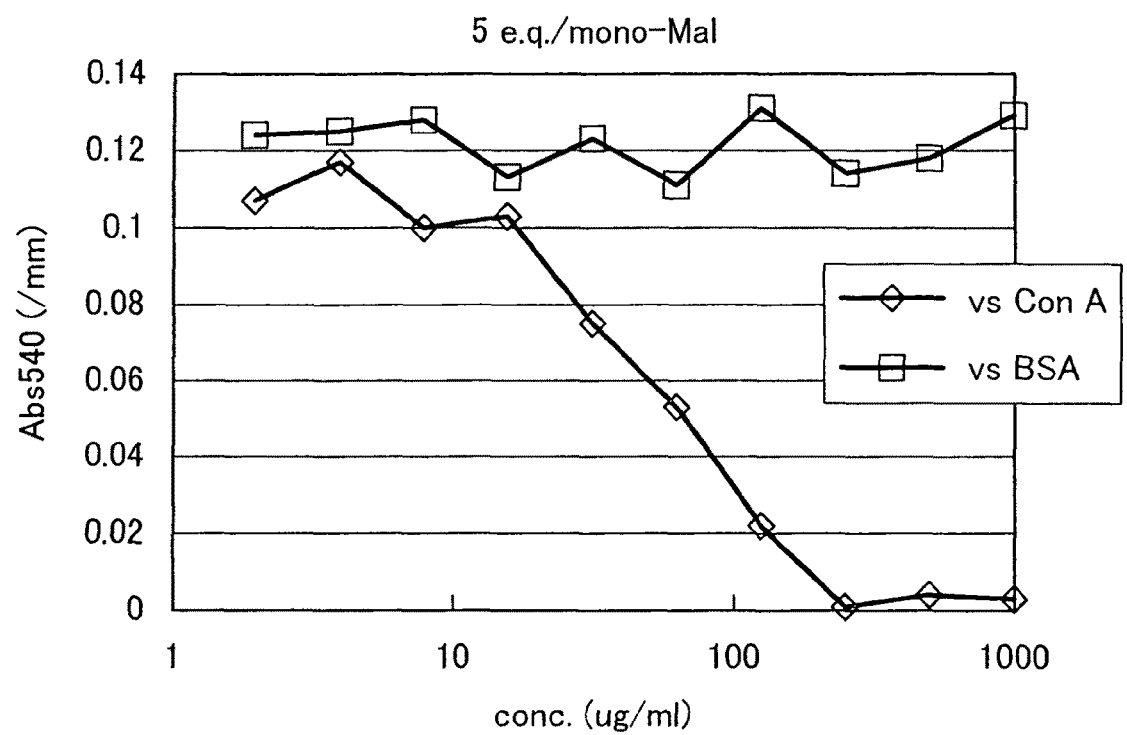
FIG. 6 is an ultraviolet-visible absorption spectrum showing sugar-protein interaction between maltose and ConA and sugar-protein interaction between maltose and BSA.
Figure 7:
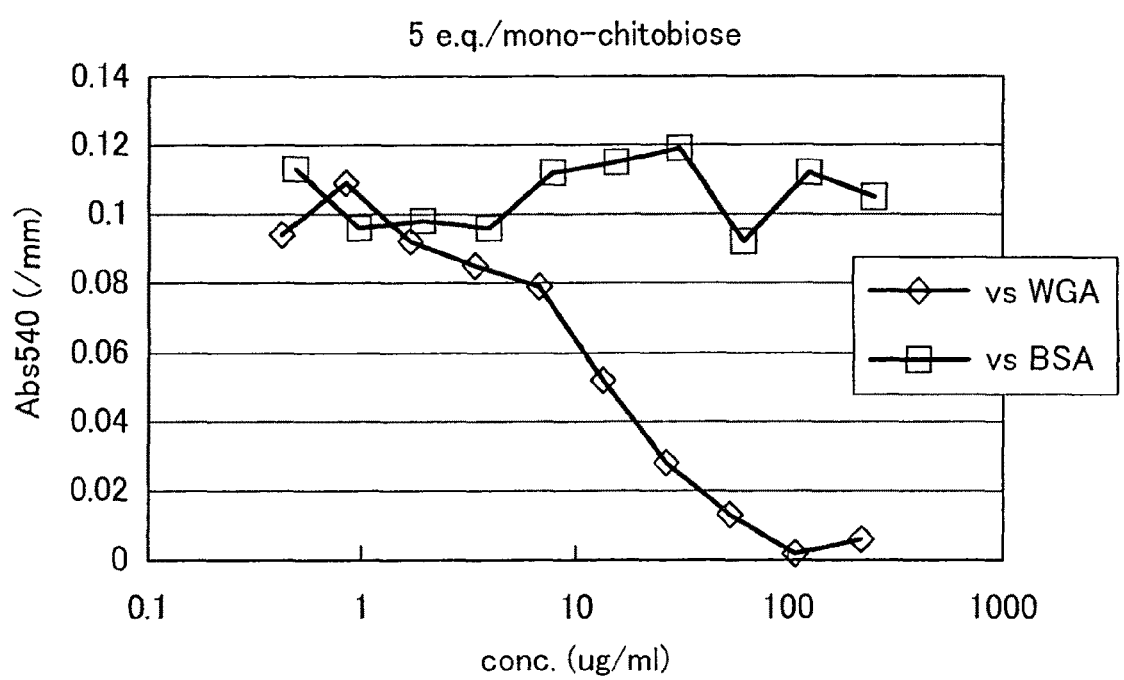
FIG. 7 is an ultraviolet-visible absorption spectrum showing sugar-protein interaction between chitobiose and WGA and sugar-protein interaction between chitobiose and BSA.

FIG. 5 is an ultraviolet-visible absorption spectrum showing sugar-protein interactions between lactose and RCA120 and between lactose and BSA. FIG. 6 is an ultraviolet-visible absorption spectrum showing sugar-protein interactions between maltose and ConA and between maltose and BSA. FIG. 7 is an ultraviolet-visible absorption spectrum showing sugar-protein interactions between chitobiose and WGA and between chitobiose and BSA.

The finding from FIG. 5 is as follows: In a case where RCA120 was used, a sugar-protein interactant of lactose and RCA120 was produced by sugar-protein interaction and was an aggregate depending upon a concentration of RCA120, whereby red-purple color (absorption at approximately 540 nm) derived from the colloid solution of lactose-immobilized gold nanoparticles disappeared.

On the other hand, in a case where the protein (BSA) that does not bind specifically to lactose was added, no aggregation occurred and ultraviolet-visible absorption spectrum remained almost unchanged.

FIG. 6 shows the results obtained in a case where ConA and maltose were used, and the results are similar to those shown in FIG. 2.

The finding from FIG. 7 was as follows: In a case where WGA was used, a sugar-protein interactant of chitobiose and WGA was produced by sugar-protein interaction and was an aggregate depending upon a concentration of WGA, whereby red-purple color (absorption at approximately 540 nm) derived from the colloid solution of chitobiose-immobilized gold nanoparticles disappeared.

Next, it was determined whether sugar-protein interaction between lectin and lactose, maltose, or chitobiose was confirmed by SDS-PAGE.

Figure 8:
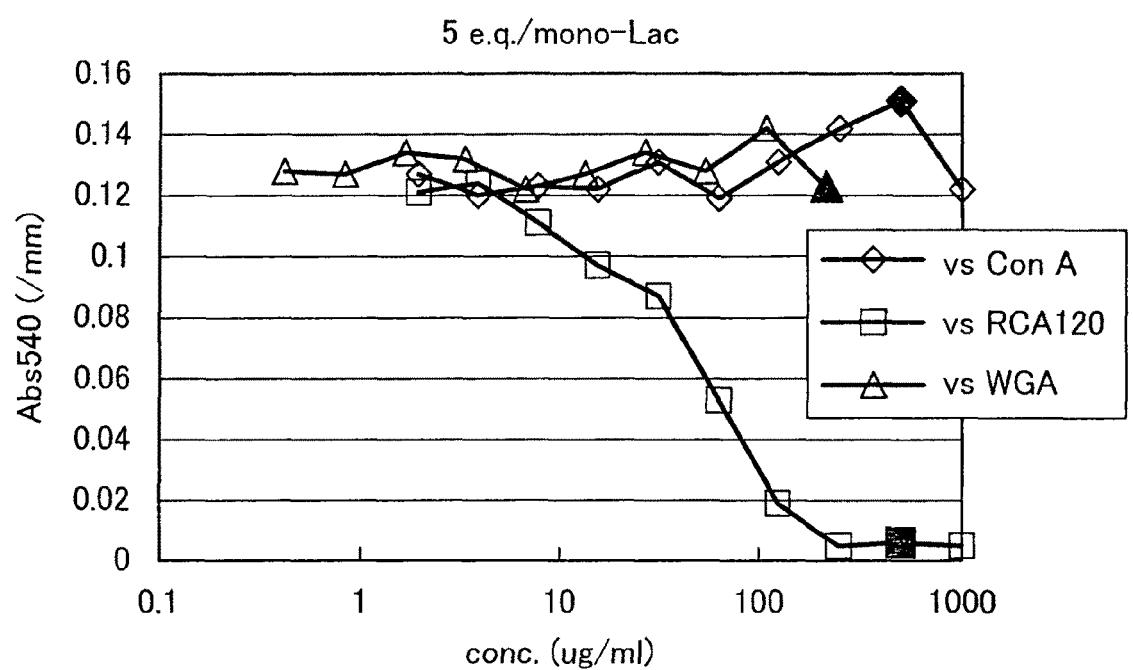
FIG. 8 is a graph showing the results of measurement of sugar-protein interactions between lactose and ConA, between lactose and RCA120, and between lactose and WGA.
Figure 9:
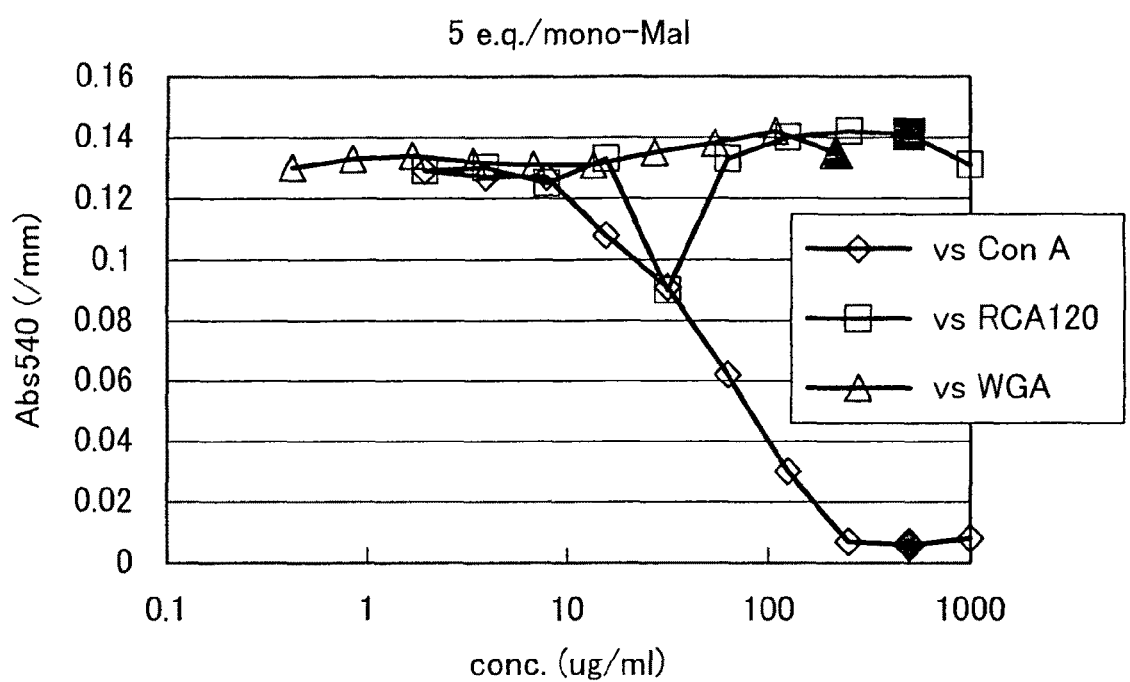
FIG. 9 is a graph showing the results of measurement of sugar-protein interactions between maltose and ConA, between maltose and RCA120, and between maltose and WGA.
Figure 10:
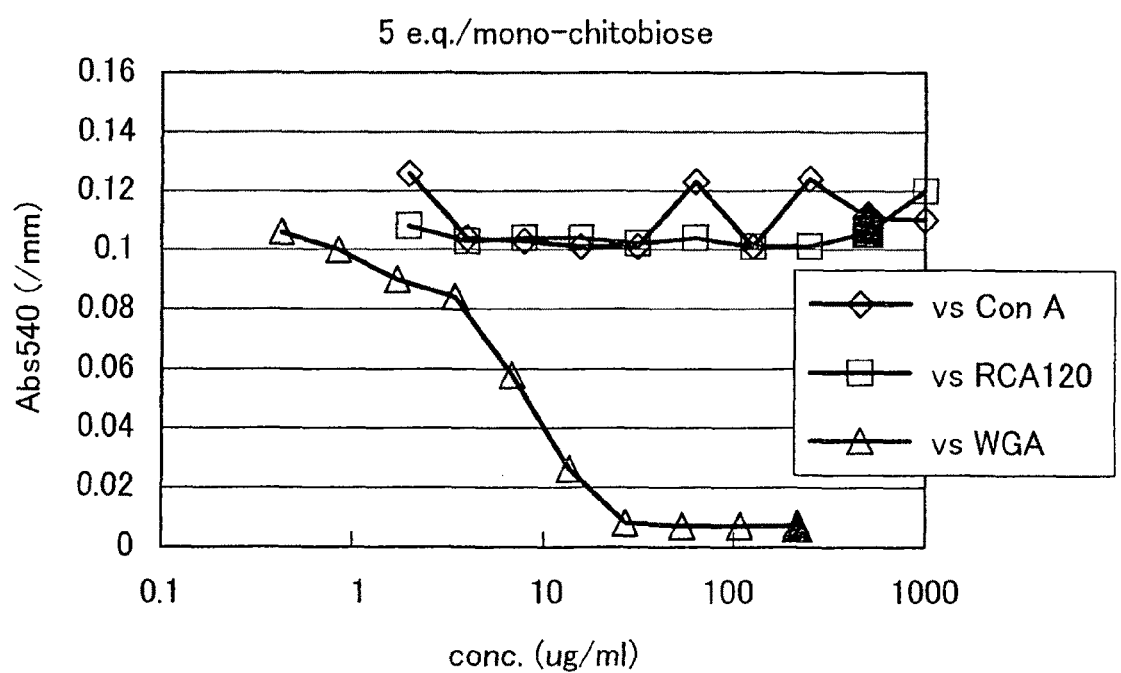
FIG. 10 is a graph showing the results of measurement of sugar-protein interactions between chitobiose and ConA, between chitobiose and RCA120, and between chitobiose and WGA.

FIG. 8 shows the results of measurement of sugar-protein interactions between lactose and ConA, between lactose and RCA120, and between lactose and WGA. FIG. 9 shows the results of measurement of sugar-protein interactions between maltose and ConA, between maltose and RCA120, and between maltose and WGA. FIG. 10 shows the results of measurement of sugar-protein interactions between chitobiose and ConA, between chitobiose and RCA120, and between chitobiose and WGA. Samples corresponding to black points shown in FIGS. 8 through 10 were subjected to SDA-PAGE. SDS-PAGE was carried out by using 15% acrylamide.

Figure 11:
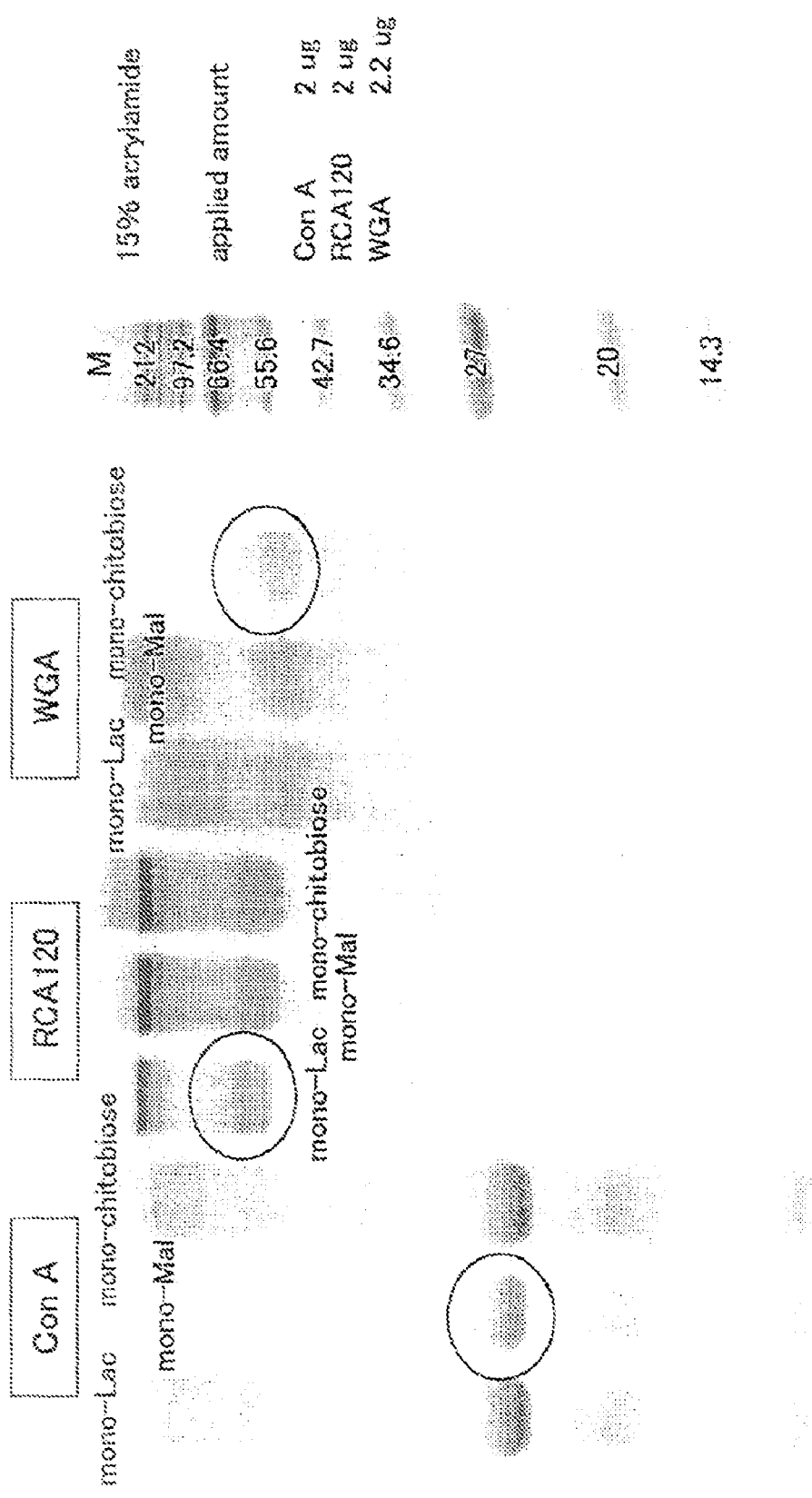
FIG. 11 is an illustration showing the results of SDS-PAGE confirming sugar-protein interactions between lectin and lactose, between lectin and maltose, and lectin and chitobiose.

FIG. 11 is a photograph showing results of SDS-PAGE. In FIG. 11, among three lanes below "ConA", lane "mono-Lac" represents a mixture of lactose and ConA, lane "mono-chitobiose" represents a mixture of chitobiose and ConA. Since no sugar-protein interactants (aggregates) were generated from these two mixtures as shown in FIGS. 8 and 10, the colloids remained highly colored in the area from the top of the lane to the band.

On the other hand, lane "mono-Mal" represents a mixture of maltose and ConA. Since a sugar-protein interactant was generated from this mixture as shown in FIG. 9, color of the colloids did not remain in the area from the top of the lane to the band, and a band of ConA becomes less dense. Thus, it was proved in the present example that sugar-protein interaction was confirmed by SDS-PAGE.

Similarly, in FIG. 11, it is determined that a sugar-protein interactant was generated in lane "mono-Lac" among three lanes below "RCA120". In FIG. 11, it is determined that a sugar-protein interactant was generated in lane "mono-GlcNAc" among three lanes below "WGA". It should be noted that lane "M" represents molecular weight marker.

Example 5

Recovery of Proteins from Sugar-Protein Interactants

The present example proves that it is possible to recover proteins by using sugar-protein interactants other than the products described in Example 3.

First, 25 µl of PBS-T (0.05%) solution containing RCA120 at 250 µg/ml was placed in an Eppendorf tube. To the solution was added 25 µl of the colloid solution of lactose-immobilized gold nanoparticles which was prepared in Example 4. Then, a mixture solution was vortexed for at least 10 seconds. Thereafter, the resulting mixture solution was left for approximately 2 hours, and a sugar-protein interactant (lactose-RCA interactant) was precipitated out of the mixture solution by centrifugation. Then, supernatant thereof was removed, and the sugar-protein interactant was washed with PBS-T (0.05%) solution and water several times. After the washing, 50 µl of galactose solution at a concentration shown in Table 1 was added to the sugar-protein interactant, and the resulting mixture solution was left for approximately 2 hours. The results were evaluated by visual observation and UV-Vis measurement.

TABLE 1

| Concentration of galactose added | Degree of dissociation |
| --- | --- |
| 200 mM | ⊚ |
| 100 mM | ⊚ |
| 50 mM | ○ |
| 25 mM | ○ |
| 12.5 mM | Δ |
| 6.25 mM | Δ |
| 3.125 mM | X |
| 1.5625 mM | X |

Table 1 shows the results of visual observation of RCA120 dissociation from the lactose-RCA120 interactant. As shown in Table 1, excellent RCA120 dissociation was observed when a solution of 25 mM or more galactose was used.

In Tables 1 and 2, ⊚ represents that lectin was completely dissociated, ○ represents that lectin was almost completely dissociated, Δ represents that lectin was dissociated with residual sugar-protein interactant (aggregate), and X represents that the lactose-RCA120 interactant kept in aggregated state, and lectin was not dissociated therefrom.

Figure 12:
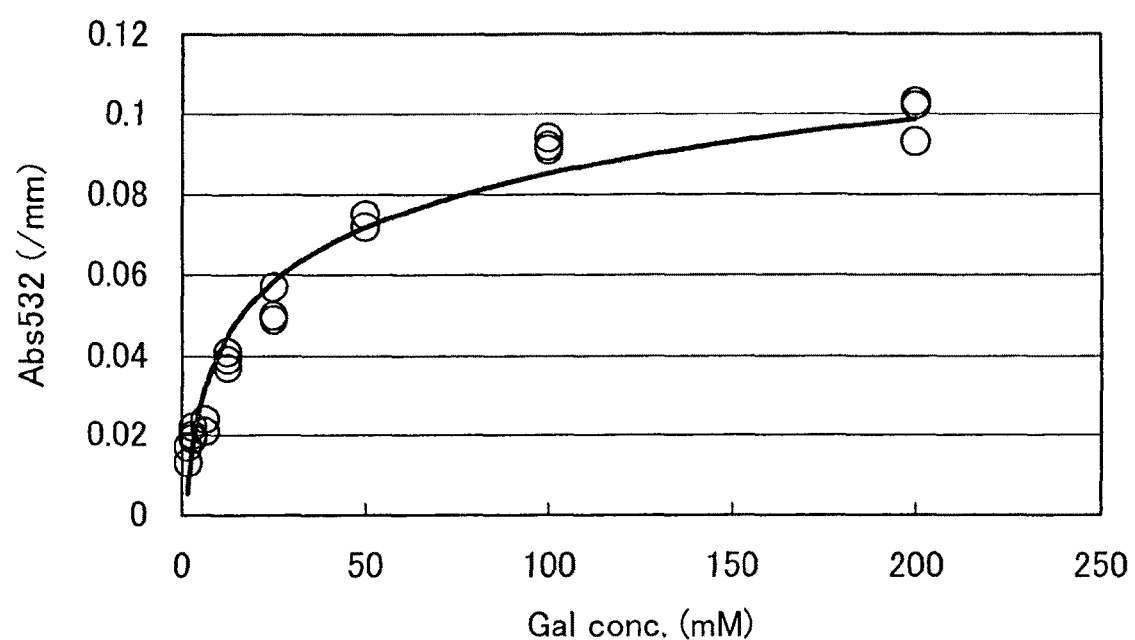
FIG. 12 is a graph showing the degrees of dissociation from a lactose-RCA120 interactant in response to changes in concentration of galactose for use in dissociation, by taking an ultraviolet-visible absorption spectrum (532 nm) at a longitudinal axis.

FIG. 12 is a graph showing the degrees of dissociation from a lactose-RCA120 interactant in response to changes in concentration of galactose for use in dissociation, by taking an ultraviolet-visible absorption spectrum (532 nm) at a longitudinal axis. With the increase of a concentration of galactose added in the solution, the amount of RCA120 dissociated and dissolved in the colloid solution increased, and an ultraviolet-visible absorption spectrum (532 nm) increased accordingly.

Figure 13:
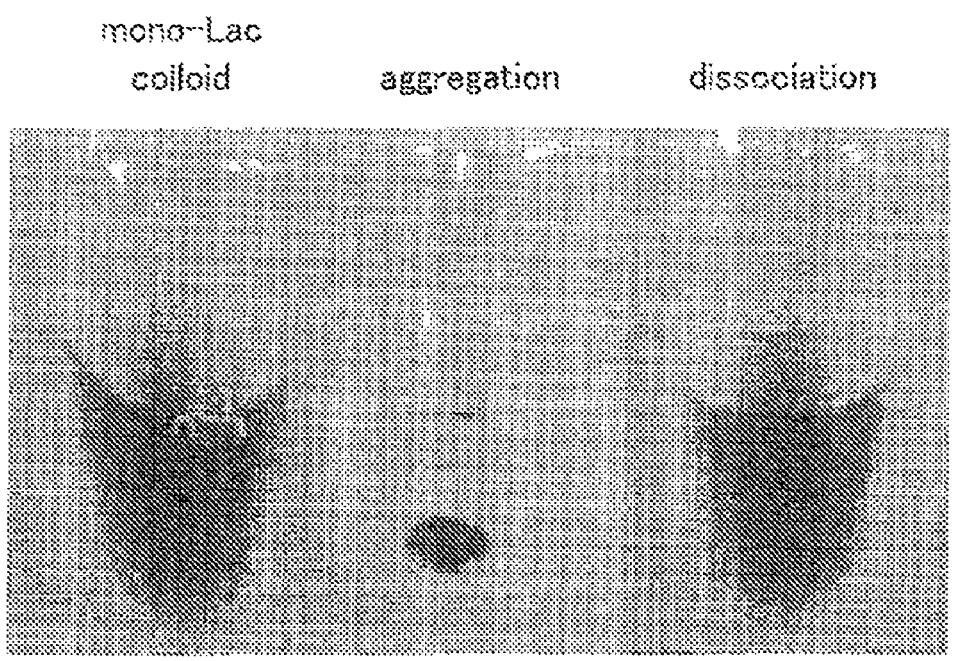
FIG. 13 is an illustration showing, from the left thereof, a photograph of a colloid solution of lactose-immobilized gold nanoparticles, a photograph of a lactose-RCA120 interactant that is an aggregate caused by sugar-protein interaction, and a photograph of dissociation of RCA120 from the lactose-RCA120 interactant by addition of a solution of 100 mM galactose to the lactose-RCA120 interactant.

FIG. 13 shows, from the left thereof, a photograph of the colloid solution of lactose-immobilized gold nanoparticles, a photograph of a lactose-RCA120 interactant that is an aggregate caused by sugar-protein interaction, and a photograph of dissociation of RCA120 from the lactose-RCA120 interactant by addition of a solution of 100 mM galactose to the lactose-RCA120 interactant. As shown in FIG. 13, even when lactose and RCA120 were used, the sugar-protein interaction was confirmed with great ease by visual observation without labeling.

Next, experiments were conducted in a similar manner, but a solution of ConA, a colloid solution of maltose-immobilized gold nanoparticles, and a solution of glucose shown in Table 2 were used instead of the solution of RCA120, the colloid solution of lactose-immobilized metal nanoparticles, and the solution of galactose shown in Table 1, respectively. Table 2 shows the results of visual observation of ConA dissociation from the maltose-ConA interactant.

TABLE 2

| Concentration of glucose added | Degree of dissociation |
| --- | --- |
| 200 mM | ⊚ |
| 100 mM | ⊚ |
| 50 mM | ⊚ |
| 25 mM | Δ |
| 12.5 mM | Δ |
| 6.25 mM | X |
| 3.125 mM | X |
| 1.5625 mM | X |

Figure 14:
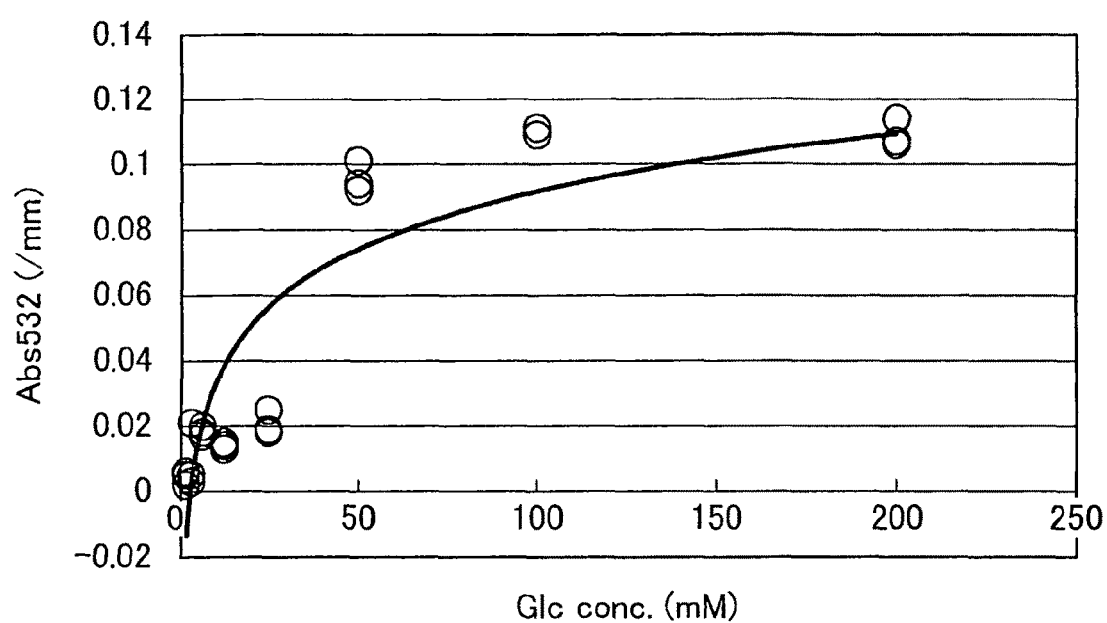
FIG. 14 is a graph showing the degrees of dissociation from a maltose-ConA interactant in response to changes in concentration of glucose for use in dissociation, by taking an ultraviolet-visible absorption spectrum (532 nm) at a longitudinal axis.

As shown in Table 2, excellent ConA dissociation was observed in a case where a solution of 50 mM or more galactose was used. FIG. 14 is a graph showing the degrees of dissociation from a maltose-ConA interactant in response to changes in concentration of glucose for use in dissociation, by taking an ultraviolet-visible absorption spectrum (532 nm) at a longitudinal axis. With the increase of a concentration of the solution of glucose added, the amount of ConA which was dissociated and dissolved in the colloid solution increased, and ultraviolet-visible absorption spectrum (532 nm) increased accordingly.

Figure 15:
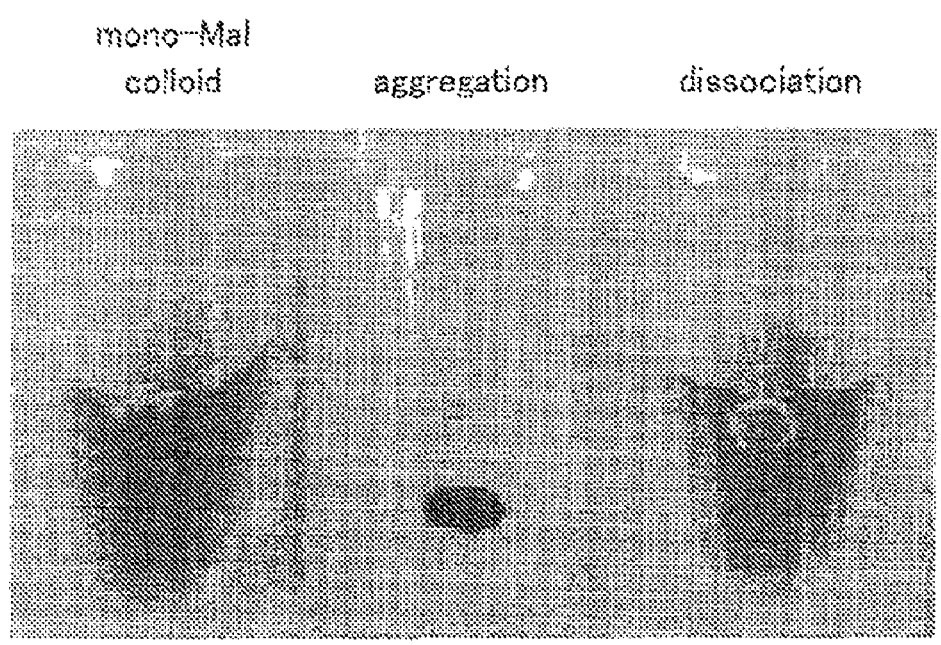
FIG. 15 is an illustration showing, from the left thereof, a photograph of a colloid solution of maltose-immobilized gold nanoparticles, a photograph of a maltose-ConA interactant that is an aggregate caused by sugar-protein interaction, and a photograph of dissociation of ConA from the maltose-ConA interactant by addition of a solution of 100 mM glucose to the maltose-ConA interactant.

FIG. 15 shows, from the left thereof, a photograph of the colloid solution of maltose-immobilized gold nanoparticles, a photograph of a maltose-ConA interactant that is an aggregate caused by sugar-protein interaction, and a photograph of dissociation of ConA from the maltose-ConA interactant by addition of a solution of 100 mM glucose to the maltose-ConA interactant. As shown in FIG. 13, even when maltose and ConA were used, the sugar-protein interaction was confirmed with great ease by visual observation without labeling.

Figure 16:
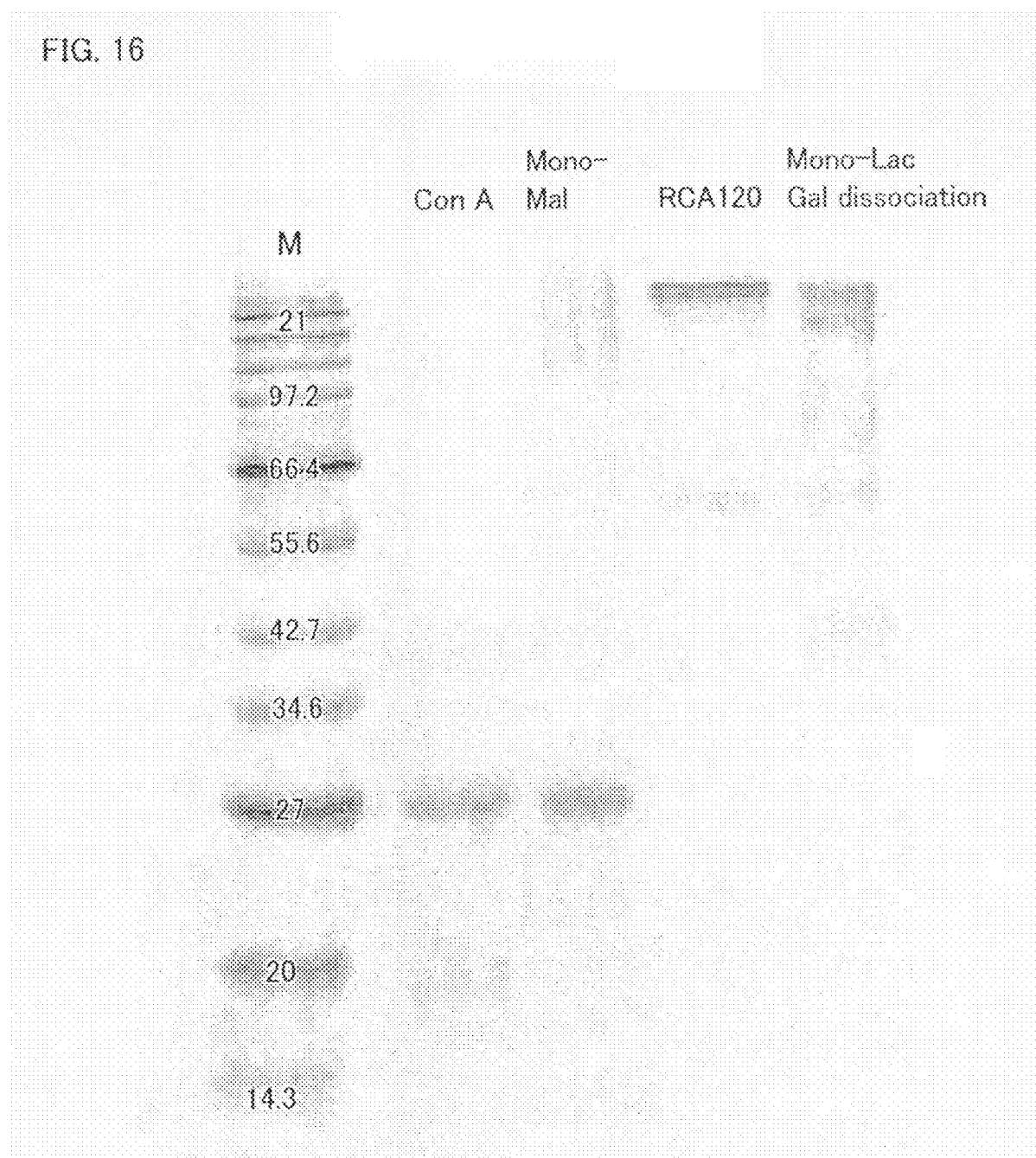
FIG. 16 is an illustration of the result of SDS-PAGE to which the colloid solution of lactose-immobilized gold nanoparticles after the dissociation of RCA120, shown in FIG. 13, was subjected, and the result of SDS-PAGE to which the colloid solution of maltose-immobilized gold nanoparticles after the dissociation of ConA, shown in FIG. 15, was subjected.

FIG. 16 shows the result of SDS-PAGE to which the colloid solution of lactose-immobilized gold nanoparticles after the dissociation of RCA120, shown in FIG. 13, was subjected, and the result of SDS-PAGE to which the colloid solution of maltose-immobilized gold nanoparticles after the dissociation of ConA, shown in FIG. 15, was subjected. In FIG. 16, lane "Mono-Lac Gal dissociation" shows the result of SDS-PAGE to which the colloid solution of lactose-immobilized gold nanoparticles after the dissociation of RCA120 was subjected. From the fact that a band was obtained at the same position as that of a RCA120 sample, it is clear that RCA120 was dissociated from the lactose-RCA120 interactant and returned to the colloid solution of lactose-immobilized gold nanoparticles.

Furthermore, lane "Mono-Mal" shows the result of SDS-PAGE to which the colloid solution of maltose-immobilized gold nanoparticles after the dissociation of ConA was subjected. From the fact that a band was obtained at the same position as that of a ConA sample, it is clear that ConA was dissociated from the maltose-ConA interactant and returned to the colloid solution of maltose-immobilized gold nanoparticles.

Example 6

Evaluation of Protein Retention Capability of the Colloid Solutions

In the present example, the experiments below were conducted for the purpose of evaluating the amounts of proteins retainable in the colloid solutions of sugar-immobilized gold nanoparticles by SDS-PAGE.

By using each of lectins, i.e. ConA, RCA120, and WGA as proteins, five 100 µl of PBS-T (0.05%) solutions were prepared in Eppendorf tubes so that the protein is contained therein at 10 μM, 8 μM, 6 μM, 4 μM, and 2 μM concentrations. As the colloid solution of sugar-immobilized gold nanoparticles (hereinafter simply referred to as "colloid solution"), a colloid solution of maltose-immobilized gold nanoparticles, lactose-immobilized gold nanoparticles, and chitobiose-immobilized gold nanoparticles (absorbance of 0.3 mm at 525 nm) were used. 100 μl of the colloid solution of maltose-immobilized gold nanoparticles was added to the ConA-containing PBS-T (0.05%) solution. 100 μl of the colloid solution of lactose-immobilized gold nanoparticles was added to the RCA120-containing PBS-T (0.05%) solution. 100 μl of the colloid solution of chitobiose-immobilized gold nanoparticles was added to the WGA-containing PBS-T (0.05%) solution. In this manner, the mixture solutions of the colloid solutions and the protein-containing solutions were prepared. Therefore, final concentrations of a protein in the mixture solutions were 5 μM, 4 μM, 3 μM, 2 μM, and 1 μM. Thereafter, each of the mixture solutions in the Eppendorf tubes was vigorously vortexed for 10 seconds, and then slowly stirred for 1 hour.

Subsequently, the solution in the Eppendorf tube was treated in a centrifugal separator at 10 krpm for 10 seconds. After the centrifugation, resulting supernatant was removed, and an aggregate was washed with PBS-T (0.05%). The aggregate was centrifuged at 10 krpm for 10 seconds, and resulting supernatant was removed. To the obtained aggregate, was added 100 μl of 200 mM glucose aqueous solution, and the resulting solution was left for approximately 1 hour.

Next, to the resulting solution was added 1 μl of 1N hydrochloric acid. After the aggregate was completely dissolved in the solution, the solution was collected from the tube (protein dissociation solution).

Figure 17:
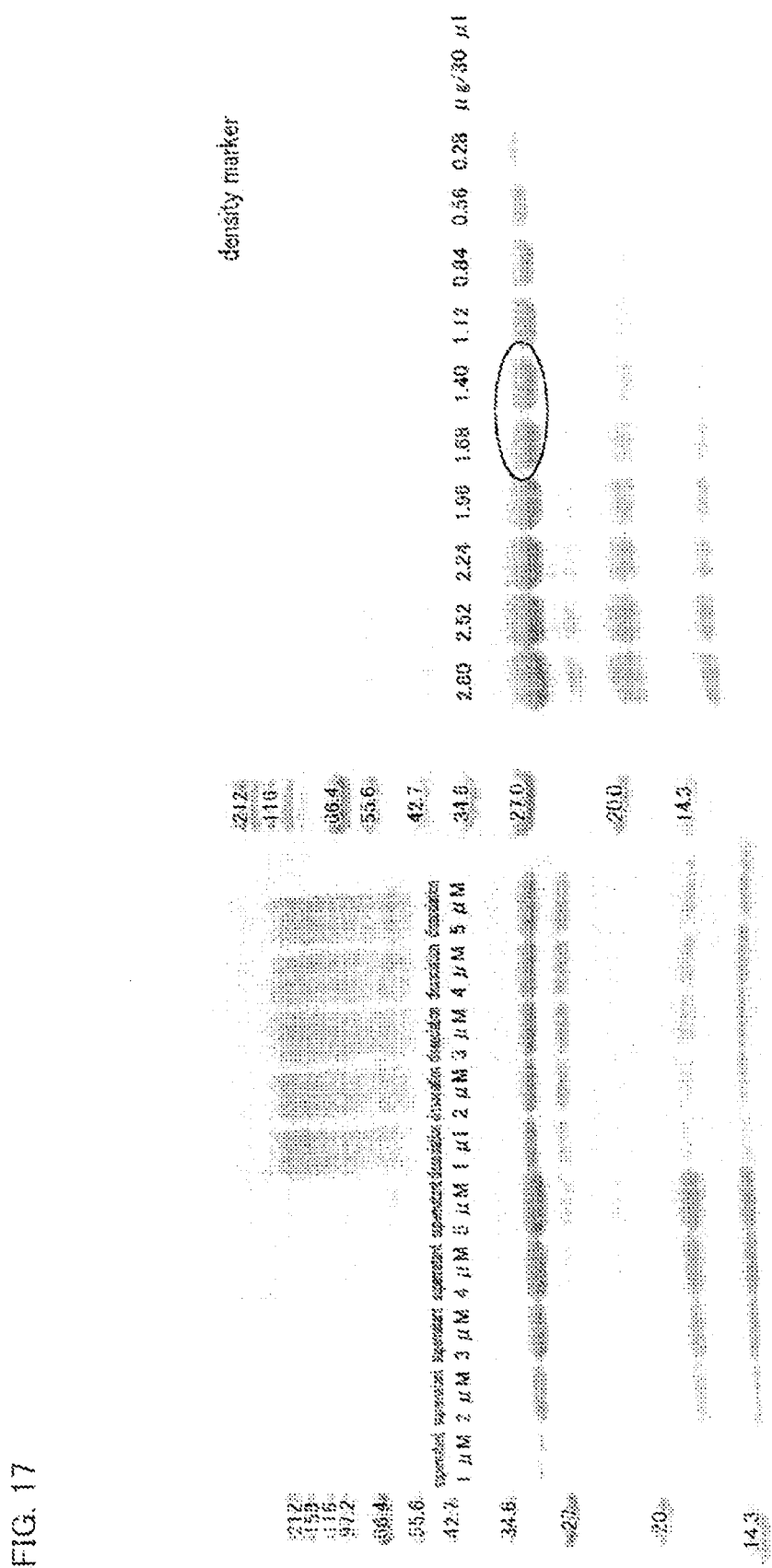
FIG. 17 is an illustration of the results of SDS-PAGE showing ConA retention capability of maltose-immobilized gold nanoparticles.
Figure 18:
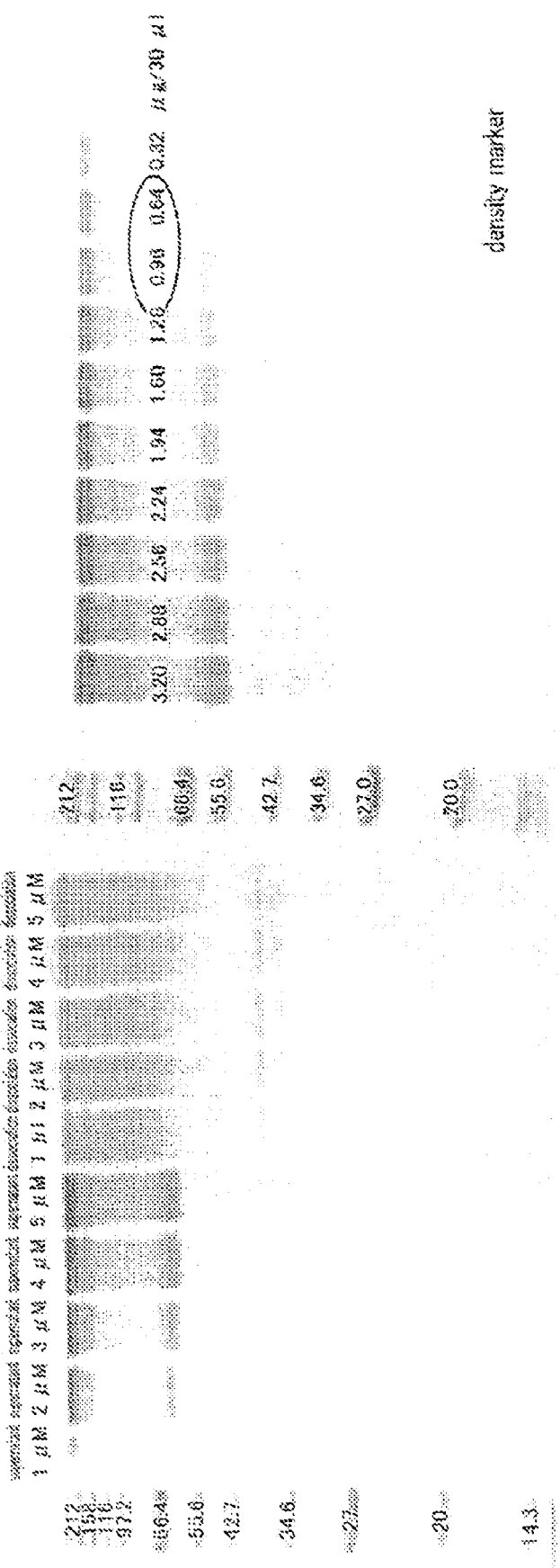
FIG. 18 is an illustration of the results of SDS-PAGE showing RCA120 retention capability of lactose-immobilized gold nanoparticles.

FIGS. 17 and 18 show the results of SDS-PAGE. FIG. 17 shows the results of SDS-PAGE for the evaluation of ConA retention capability of the maltose-immobilized gold nanoparticles. As shown in FIG. 17, bands for the supernatants are dense in a concentration-dependent manner. In the case of the protein dissociation solutions, densities of bands for 2 μM or more are almost the same, although band for 1 μM is less dense than the bands for 2 μM or more.

Thus, the ConA retention capability of the maltose-immobilized gold nanoparticles contained in the above mixture solution is considered to be 2 μM at the most. It should be noted that the "band for 1 μM", for example, is the band which was obtained after the protein dissociation solution obtained from the above mixture solution with a final concentration of 1 μM was subjected to SDS-PAGE.

FIG. 18 shows the results of SDS-PAGE for the evaluation of RCA120 retention capability of the lactose-immobilized gold nanoparticles. As shown in FIG. 18, bands for the supernatants are dense in a concentration-dependent manner. On the other hand, in the case of the protein dissociation solutions, densities of bands for 2 μM or more are almost the same, although band for 1 μM is less dense than the bands for 2 μM or more. Thus, the RCA120 retention capability of the lactose-immobilized gold nanoparticles contained in the above mixture solution is considered to be 2 μM at the most.

Example 7

Inhibition of Sugar-Protein Interaction by Using Sugar Chain

As described previously, a more detailed analysis of the protein would be possible if aggregation due to the sugar-protein interaction could be inhibited by addition of various types of sugar chains that are recognizable by the protein in the reaction of the protein with the sugar-immobilized metal nanoparticle. For example, it would be possible to perform a functional analysis that determines which sugar chain is more apt to form a strong bond with the protein, and the like analysis.

In view of this, in the present example, experiments to confirm inhibition of sugar-protein interaction were conducted by using various types of sugar chains.

A colloid solution of sugar-immobilized gold nanoparticles was prepared by using PBS-T (0.05%) so that absorbance at 525 nm is 0.6 (/mm). As the sugar-immobilized gold nanoparticles, maltose-immobilized gold nanoparticles or lactose-immobilized gold nanoparticles were used. A PBS-T (0.05%) solution containing glucose, maltose, GlcNAc, galactose, or lactose as a sugar chain at a concentration of 400 mM was prepared.

First, a PBS-T (0.05%) solution containing ConA or RCA120 at a concentration of 2 μM was prepared as a lectin solution, and the lectin solution was introduced to 96-well titer plate by adding 10 μl in each well. Then, a glucose solution, a maltose solution, or a GlcNAc solution was added to a ConA-added well by 20 μl in each well. A galactose solution or a lactose solution was added to a RCA120-added well by 20 μl in each well. The resulting solutions were stirred at a room temperature for 1 hour. Subsequently, 10 μl of maltose-immobilized gold nanoparticles was added to the ConA-added well, and 10 μl of lactose-immobilized gold nanoparticles was added to the RCA120-added well. The resulting solutions were stirred at a room temperature for 1 hour. After the stirring, absorbance of the stirred solutions at 525 nm was measured.

Figure 19:
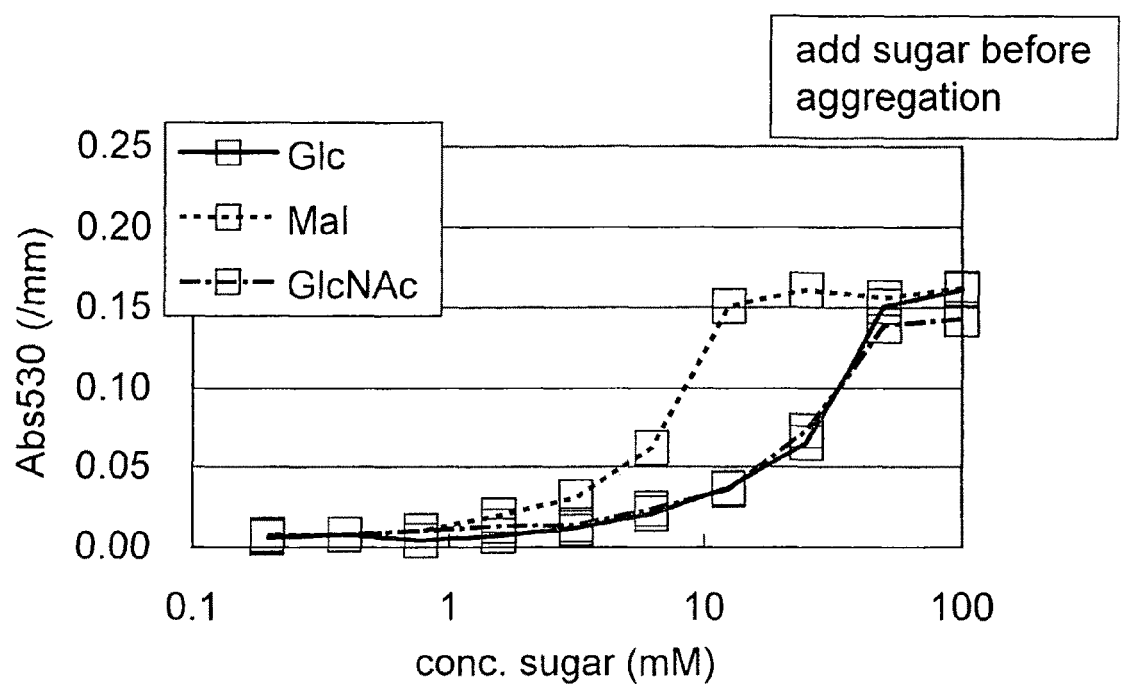
FIG. 19 is a graph showing the results of absorbance measurement obtained as a result of aggregation inhibition in a case where a colloid solution is a maltose-immobilized gold nanoparticles, a lectin is ConA, and a sugar chain is a glucose, maltose, or GlcNAc.

FIG. 19 shows absorbance measurement results obtained by using a colloid solution of maltose-immobilized gold nanoparticles as a colloidal solution, ConA as a lectin, and a chain of glucose, maltose, or GlcNAc as a sugar chain.

Table 3 shows 50% inhibitory concentrations ($IC_{50}$) of glucose, maltose, and GlcNAc, calculated from the results shown in FIG. 19. Values below the "after" column are $IC_{50}$ obtained in a case where the sugar chain was added to an aggregate of the lectin and the colloid solution. Values below the "before" column are $IC_{50}$ obtained in a case where the colloid solution was added to the admixture of the lectin and the sugar chain.

TABLE 3

|  | $IC_{50}$ (mM) | |
| --- | --- | --- |
| Sugar | after | before |
| Glucose | 43.7 | 27.7 |
| Maltose | 32.5 | 3.0 |
| GlcNAc | 80.1 | 22.9 |

Example 8

Confirmation of Sugar-Protein Interaction by Dot Blotting

In the present example, a study was conducted on the possibility of confirmation of sugar-protein interaction by dot blotting.

First, a PBS-T (0.05%) solution containing ConA, RCA120, or WGA at a concentration of 1000 μg/ml was spotted by 0.5 μl on a membrane (Biodyne® A; pore diameter of 0.2 μm; material: nylon 6,6; manufactured by Nihon Pall Ltd. (BNRG3R)). The membrane was left until it is completely dried. Then, the membrane was immersed in a colloid solution and left for approximately 1 hour. Thereafter, the membrane was taken out of the colloid solution, washed with water, and dried in air for spot checking. The colloidal solution was a colloid solution of maltose-immobilized gold nanoparticles, a colloid solution of lactose-immobilized gold nanoparticles, or a colloid solution of chitobiose-immobilized gold nanoparticles. The colloid solution was prepared by using PBS-T (0.05%) so that absorbance at 525 nm is 0.3, 0.15, or 0.03 (/mm).

Figure 20:
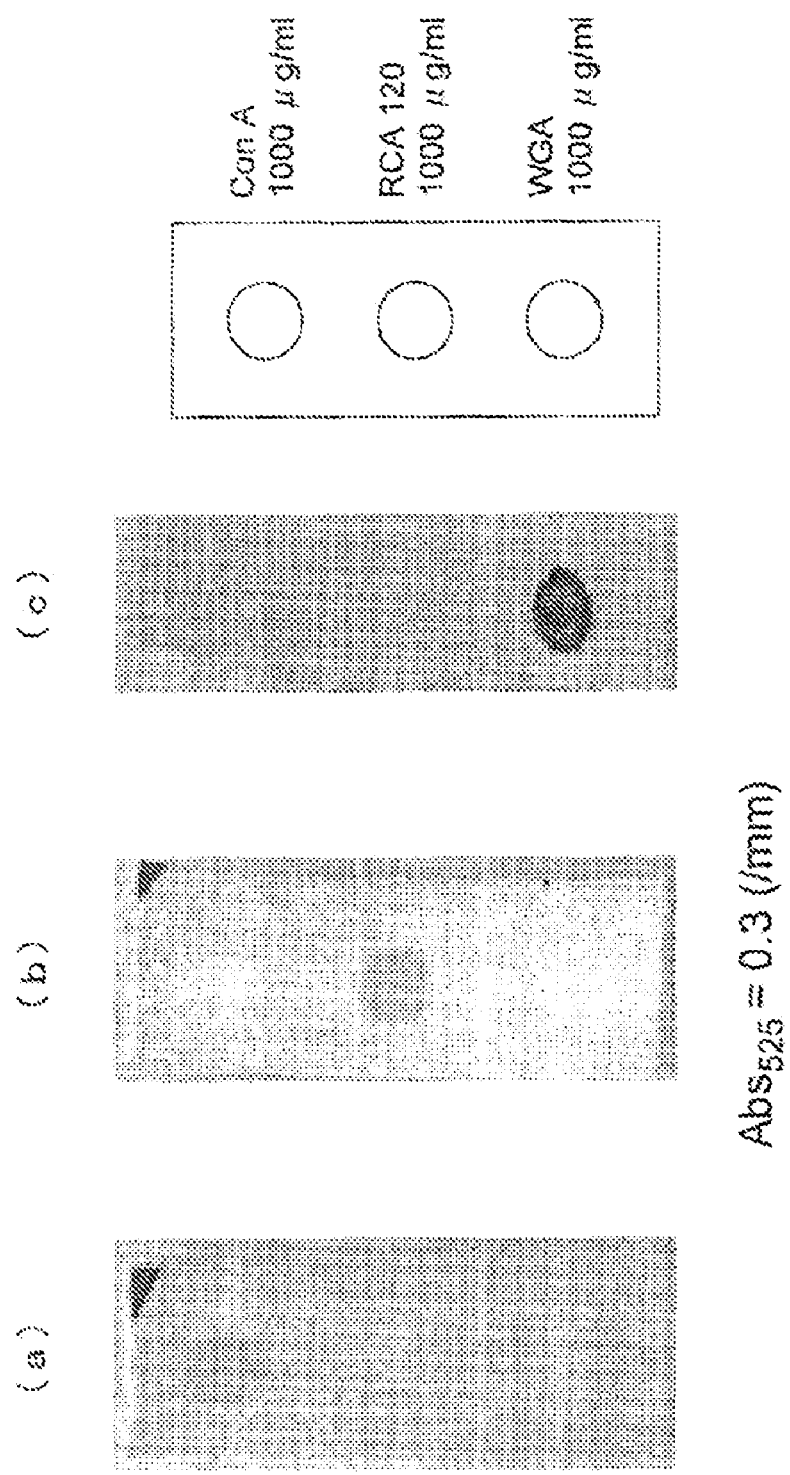
FIG. 20 is an illustration showing the results of dot blotting obtained by using a colloid solution in which an absorbance at 525 nm (Abs 525) is 0.3 (/mm).

The results are shown in FIG. 20. FIG. 20 shows the results of dot blotting obtained by using a colloid solution in which absorbance at 525 nm (Abs 525) is 0.3 (/mm). As shown in FIG. 20(a), it was confirmed that the maltose-immobilized gold nanoparticles specifically recognized ConA. As shown in FIG. 20(b), the lactose-immobilized gold nanoparticles specifically recognized RCA120. As shown in FIG. 20(c), the chitobiose-immobilized gold nanoparticles specifically recognized WGA. That is, it was found that the sugar-protein interaction is confirmed by dot blotting.

Table 4 shows sugar-protein interactions between various types of sugar-immobilized gold nanoparticles and various types of lectins. In Table 4, "+++" represents that 100% of sugar-immobilized gold nanoparticles under test aggregated. "++" represents that 50% of sugar-immobilized gold nanoparticles under test aggregated. "+" represents that 10% of sugar-immobilized gold nanoparticles under test aggregated. In Table 4, "−" represents that less than 10% of sugar-immobilized gold nanoparticles under test aggregated.

In Table 4, "hepalin partial structure" denotes GlcNS6Sα1-4IdoA2Sβ1-6Glc.

TABLE 4

|  | ConA Concanavalin A | RCA120 Caster bean lectin | WGA Wheat germ lectin | BPA Dolichos biflorus lectin | MAM Maackia amurensis lectin | SSA Sambucus sieboldiana lectin |
|---|---|---|---|---|---|---|
| Maltose | +++ | − | − | − | − | − |
| Maltotriose | +++ | − | − | − | − | − |
| Isomaltotriose | +++ | − | − | − | − | − |
| Cellobiose | − | − | − | − | − | − |
| Gentibiose | − | − | − | − | − | − |
| Melibiose | − | +++ | − | +++ | − | + |
| Lactose | − | +++ | − | − | − | − |
| Mannobiose | +++ | − | − | − | − | − |
| Fucosyllactose | − | − | − | − | − | − |
| Mannotriose | +++ | − | − | − | − | − |
| Chitobiose | − | − | +++ | ++ | − | − |
| Globobiose | − | − | +++ | +++ | − | − |
| Hepalin Partial Structure | − | − | − | − | − | − |

|  | PSA Pisum sativum lectin | PNA peanut lectin | LCA lentil lectin | JAC Jacalin | GS-II Griffonia simplicifolia lectin | UEA-I Ulex europaeus lectin | BSA Bovine serum albumin |
|---|---|---|---|---|---|---|---|
| Maltose | − | − | − | − | ++ | − | − |
| Maltotriose | − | − | − | − | − | − | − |
| Isomaltotriose | − | − | − | − | − | − | − |
| Cellobiose | − | − | − | − | − | − | − |
| Gentibiose | − | − | − | − | − | − | − |
| Melibiose | − | +++ | − | +++ | − | − | − |
| Lactose | − | +++ | − | − | − | − | − |
| Mannobiose | +++ | − | − | − | − | − | − |
| Fucosyllactose | − | − | − | − | − | +++ | − |
| Mannotriose | − | − | − | − | − | − | − |
| Chitobiose | − | − | − | − | + | − | − |
| Globobiose | − | + | − | − | − | − | − |
| Hepalin Partial Structure | − | − | − | − | − | − | − |

+++: 100% aggregation
++: 50% aggregation
+: 10% aggregation
−: less than 10% aggregation Table 5 shows sugar chains which lectins shown in Table 4 can recognize.

TABLE 5

| Lectin | Abbreviation | Recognized sugar chain | Manufacturer |
|---|---|---|---|
| Concanavalin A | ConA | Mannose, glucose | EY Laboratories |
| Caster bean lection | RCA120 | Galactose | Seikagaku Corporation |
| Wheat germ lectin | WGA | N-acetylglucosamine | Seikagaku Corporation |
| Dolichos biflorus lectin | BPA | N-acetylgalactosamine | EY Laboratories |
| Maackia amurensis lectin | MAM | Sialic acid | Seikagaku Corporation |
| Sambucus sieboldiana lectin | SSA | Sialic acid | Seikagaku Corporation |
| Pisum sativum lectin | PSA | Glucose, mannose, fucose | Seikagaku Corporation |

TABLE 5-continued

| Lectin | Abbreviation | Recognized sugar chain | Manufacturer |
|---|---|---|---|
| Peanut lectin | PNA | Galactose | Seikagaku Corporation |
| Lentil lectin | LCA | Glucose, mannose | Seikagaku Corporation |
| Jacalin | JAC | Galactose, sialic acid | Seikagaku Corporation |
| Griffonia simplicifolia lectin | GS-II | N-acetylglucosamine | Seikagaku Corporation |
| Ulex europaeus lectin | UEA-I | Fucose | EY Laboratories |
| Bovine serum albumin | BSA | None | EY Laboratories |

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, a sugar-immobilized metal nanoparticle of the present invention is stable, can be prepared simply by mixing a ligand complex with an arbitrary metal, and therefore can immobilize a sugar chain easily. A method for measuring sugar-protein interaction according to the present invention is such that an aggregate through interaction of sugar and protein is formed simply by mixing a solution containing the sugar-immobilized metal nanoparticle of the present invention with a protein that recognizes a sugar situated at the end of the sugar-immobilized metal nanoparticle. Therefore, it is possible to easily measure sugar-protein interaction by visual observation without labeling.

Furthermore, a method for recovering a protein from a sugar-protein interactant according to the present invention is such that interaction of sugar and protein is changed by making an admixture solution acidic and mixing into a solution containing a sugar chain that is recognizable by a protein. Therefore, it is possible to easily recover a protein from a sugar-protein interactant through interaction of sugar and protein.

For this reason, the present invention can be used in functional analysis of sugars and proteins and test and diagnosis applications. It is expected that the present invention contributes for pharmaceutical development and elucidation of life phenomena. The present invention is therefore applicable to a wide range of industry, including medical industry and biotechnology industry.

The invention claimed is:

1. A sugar-immobilized metal nanoparticle, which comprises:
   a ligand complex of a structure including a linker compound comprising thioctic acid and m-phenylenediamine at a molar ratio of 1:1, and a sugar having a reducing end, the linker compound including a hydrocarbon structure which includes: a hydrocarbon inducing chain with an aromatic amino group at an end and a carbon-nitrogen bond in a backbone; and a sulfur atom, the sugar being bound to the linker compound via the amino group; and
   gold bound to the ligand complex,
   wherein the sugar-immobilized metal nanoparticle is obtained by mixing the ligand complex with a solution of a gold nanoparticle prepared by mixing sodium tetrachloroaurate (III) with sodium borohydride,
   wherein the sugar-immobilized metal nanoparticle is stable,
   wherein a solution of the sugar-immobilized metal nanoparticle contains sodium tetrachloroaurate (III) at a concentration of 0.5 mM to 4 mM, sodium borohydride at a concentration that is 3 to 10 times a molar concentration of gold ion, and the ligand complex at a concentration of 10 μM to 1000 μM, and
   wherein the sugar-immobilized metal nanoparticle forms a sugar-protein interactant through interaction of a sugar and a protein, and
   wherein the sugar-immobilized metal nanoparticle forms a colloid solution when mixed with an aqueous solution.

2. A method for measuring sugar-protein interaction, comprising the step of forming a sugar-protein interactant through interaction of sugar and protein by mixing a solution containing the sugar-immobilized metal nanoparticle of claim 1 with a protein that recognizes the sugar situated at the end of the sugar-immobilized metal nanoparticle.

3. A method for recovering a protein from a sugar-protein interactant, comprising the steps of:
   forming a sugar-protein interactant through interaction of sugar and protein by mixing a solution containing the sugar-immobilized metal nanoparticle of claim 1 with a protein that recognizes the sugar situated at the end of the sugar-immobilized metal nanoparticle; and
   adjusting a pH of an admixture solution of the sugar-protein interactant and water to 5 or less.

4. A method for recovering a protein from a sugar-protein interactant, comprising the steps of:
   forming a sugar-protein interactant through interaction of sugar and protein by mixing a solution containing the sugar-immobilized metal nanoparticle of claim 1 with a protein that recognizes the sugar situated at the end of the sugar-immobilized metal nanoparticle; and
   mixing the sugar-protein interactant with a sugar that is recognizable by the protein.

\* \* \* \* \*

UNITED STATES PATENT AND TRADEMARK OFFICE
CERTIFICATE OF CORRECTION

PATENT NO. : 8,067,393 B2 Page 1 of 1
APPLICATION NO. : 11/920878
DATED : November 29, 2011
INVENTOR(S) : Yasuo Suda et al.

It is certified that error appears in the above-identified patent and that said Letters Patent is hereby corrected as shown below:

Title Page, Item (73) Assignees: add --Yasuo Suda, Kagoshima (JP)--

Signed and Sealed this
Twenty-eighth Day of August, 2012

David J. Kappos
*Director of the United States Patent and Trademark Office*